(12) United States Patent
Mansfield et al.

(10) Patent No.: US 12,600,941 B2
(45) Date of Patent: Apr. 14, 2026

(54) METHOD FOR PRODUCING BIOMASS USING HYDROGEN-OXIDIZING BACTERIA

(71) Applicant: AERBIO A/S, Glostrup (DK)

(72) Inventors: Robert Patrick William Mansfield, Nottingham (GB); Bart Pander, Edinburgh (GB); Preben Krabben, Didcot (GB); Peter Nicholas Rowe, Voorschoten (NL)

(73) Assignee: AERBIO AIS (formerly Marsor DK ApS), Glostrup (DK)

( * ) Notice: Subject to any disclaimer, the term of this patent is extended or adjusted under 35 U.S.C. 154(b) by 576 days.

(21) Appl. No.: 17/996,826

(22) PCT Filed: Apr. 26, 2021

(86) PCT No.: PCT/EP2021/060880
§ 371 (c)(1),
(2) Date: Oct. 21, 2022

(87) PCT Pub. No.: WO2021/214345
PCT Pub. Date: Oct. 28, 2021

(65) Prior Publication Data
US 2023/0203433 A1 Jun. 29, 2023

(30) Foreign Application Priority Data
Apr. 24, 2020 (GB) ..................................... 2006071

(51) Int. Cl.
*C12N 1/20* (2006.01)
*A23J 1/00* (2006.01)
(Continued)

(52) U.S. Cl.
CPC .............. *C12N 1/205* (2021.05); *A23J 1/008* (2013.01); *A23K 10/12* (2016.05); *A23K 20/147* (2016.05);
(Continued)

(58) Field of Classification Search
CPC .................................. A23J 1/008; C12N 1/20
See application file for complete search history.

(56) References Cited

U.S. PATENT DOCUMENTS 9,157,058 B2 10/2015 Dalla-Betta et al.
9,206,451 B2 12/2015 Sefton
(Continued)

FOREIGN PATENT DOCUMENTS

CN 109423452 A 3/2019
WO WO 2011/139804 A2 11/2011
(Continued)

OTHER PUBLICATIONS

Lambauer et al. "Lab-Scale Cultivation of Cupriavidus necator on Explosive Gas Mixtures: Carbon Dioxide Fixation into Polyhydroxybutyrate" Bioengineering 2022, 9, 204. https://doi.org/10.3390/bioengineering9050204 (Year: 2022).*
(Continued)

*Primary Examiner* — Michele L Jacobson
(74) *Attorney, Agent, or Firm* — Jerold I Schneider; Schneider IP Law

(57) ABSTRACT

The present invention provides a method for producing a biomass comprising at least 65% protein from hydrogen-oxidising microorganisms using one or more input streams comprising one or more gaseous substrates and a nutrient composition which are controlled and wherein the biomass is produced at a rate of more than 10 g/l/d. The produced and isolated biomass is useful as feed or to provide nutrition to one or more organisms.

16 Claims, 7 Drawing Sheets

(51) Int. Cl.

| | | |
|---|---|---|
| *A23K 10/12* | (2016.01) | |
| *A23K 20/147* | (2016.01) | |
| *A23K 50/10* | (2016.01) | |
| *A23K 50/30* | (2016.01) | |
| *A23K 50/75* | (2016.01) | |
| *A23K 50/80* | (2016.01) | |
| *C12N 1/205* | (2026.01) | |
| *C12R 1/01* | (2006.01) | |

(52) U.S. Cl.

CPC .............. *A23K 50/10* (2016.05); *A23K 50/30* (2016.05); *A23K 50/75* (2016.05); *A23K 50/80* (2016.05); *C12R 2001/01* (2021.05)

(56) References Cited

U.S. PATENT DOCUMENTS

| | | |
|---|---|---|
| 2010/0120104 A1 | 5/2010 | Reed |
| 2020/0165733 A1* | 5/2020 | Reed ........................ A61P 35/00 |

FOREIGN PATENT DOCUMENTS

| | | |
|---|---|---|
| WO | WO 2013/090769 A2 | 6/2013 |
| WO | WO 2017/165244 A1 | 9/2017 |
| WO | WO 2018/144965 A1 | 8/2018 |
| WO | WO 2019/010116 A1 | 1/2019 |

OTHER PUBLICATIONS

Casey et al. "From Knallgas Bacterium to Promising Biomanufacturing Host: The Evolution of Cupriavidus necator" in Unconventional Organisms in Biotechnology. Ed. D. Holtmann, 2025 p. 59-84 (Year: 2025).*

Volova et al.; "Characteristics of Protein Synthesized by Hydrogen-Oxidizing Microorganisms"; Applied Biochemistry and Microbiology; vol. 46 No. 6; 2010; p. 574-579.

Das et al.; "Oxya hyla hyla (Orthoptera: Acrididae) as an Alternative Protein Source for Japanese Quail"; Int'l Scholarly Research Notes; vol. 2014 Article 269810; 2014; 15 pages.

R. K. Kumar; "Flammability Limits of Hydrogen-Oxygen-Diluent Mixtures"; Journal of Fire Sciences; vol. 3; Jul.-Aug. 1985; p. 245-262.

Little et al.; "Complete Genome Sequence of Cupriavidus necator H16 (DSM 428)"; Microbiology Resource Announcements; vol. 8 Issue 37; 2019; 2 pages.

Morinaga et al.; "Growth Characteristics and Cell Composition of Alcaligenes eutrophus in Chemostat Culture"; Agriculture and Biological Chemistry; vol. 42(2); 1978; p. 439-444.

Pohlmann et al.; "Genome sequence of the bioplastic-producing "Knallgas" bacterium Ralstonia eutropha H16"; Nature Biotechnology; 2006; 7 pages.

"U.S. Soybean Meal"; https://ussec.org/wp-content/uploads/2015/10/US-Soybean-Meal-Information.pdf; U.S. Soybean Export Council; accessed Dec. 27, 2022; 4 pages.

Great Britain Patent Application No. 2006071.1; Search Report; dated Dec. 1, 2020; 7 pages.

International Patent Application No. PCT/EP2021/060880; Int'l Written Opinion; dated Jan. 2015; 6 pages.

Report to the University of Hawaii at Manoa on the Hydrogen/Oxygen Explosion of Mar. 16, 2016, Report 1: Technical Analysis of Accident—UC (University of California) Center for Laboratory Safety, Jun. 29, 2016.

Neubauer et al., The Rocky Road from Fed-Batch to Continuous Processing, Frontiers in Bioengineering and Biotechnology, (Nov. 20, 2019).

Peebo, K. & Neubauer, P., Application of Continuous Culture Methods to Recombinant Protein Production in Microorganisms (Jun. 21, 2018).

* cited by examiner

METHOD FOR PRODUCING BIOMASS USING HYDROGEN-OXIDIZING BACTERIA

CROSS-REFERENCE TO RELATED APPLICATIONS

This application is the US National Stage Application of International Patent Application No. PCT/EP2021/060880, filed Apr. 26, 2021, which claims the benefit of the priority of Great Britain Patent Application No. 2006071.1, filed Apr. 24, 2020, the disclosures of which are incorporated herein by reference in their entireties.

FIELD OF THE INVENTION

The present invention provides a method for producing a biomass comprising at least 65% protein from hydrogen-oxidising microorganisms using one or more input streams comprising one or more gaseous substrates.

BACKGROUND OF THE INVENTION

Production of protein as a food source in a more sustainable fashion is needed to reduce resource use and greenhouse gas (GHG) emissions. A growing global population puts increasing pressure on the availability of resources and the environment. Animal products such as meat, fish, milk and eggs are important dietary sources of protein, but livestock use a large area of agricultural land, energy and water. This is mainly due to the fact that animal feed consists of large quantities of plants specifically grown for this purpose. An alternative source of the protein component of animal feed or even for direct human consumption is microbial protein, which can be tailored in composition to suit specific nutritional needs. Microbial protein is considered to be a highly sustainable source of protein, due to the efficiency of land, energy, and water usage in its production.

Many industrial processes generate off-gas streams that comprise carbon dioxide among other gas components. Examples are the production of energy through combustion, lime, fertilizers, and cement, which are major sources of atmospheric carbon dioxide, as well as other GHG. Carbon oxides from industrial sources are primarily produced by the combustion of fossil fuels and/or chemicals and are classified as GHG due to their contribution to deleterious environmental conditions. Other industrial processes that include combustion of wastes are municipal solid waste, sewage sludge, plastic, tires, agricultural residues and the like, as well as coal- or gas-fired electricity plants.

Microbes require a source of carbon in order to live, grow and produce chemical products. Thus, carbon oxides derived from industrial gas effluent represent a potentially cheap, sustainable, and scalable means to obtain carbon for microbially-mediated production of food rich in protein, and a way to reduce the amount of carbon dioxide released directly into the atmosphere.

Therefore, it would be desirable to be able to convert gaseous feedstocks into a source of high-quality biomass. Accordingly, there is a need for an improved, simple, highly productive and economical process for the biological production of biomass useful as e.g. animal feed or direct human consumption.

Prior work is known relating to certain applications of chemoautotrophic microorganisms in the capture and conversion of carbon dioxide gas to fixed carbon. However, many of these approaches have suffered shortcomings that have limited the effectiveness, economic feasibility, practicality and commercial adoption of the described processes. In particular, achieving a maximal productivity rate, preferably by maintaining a high concentration of the microorganisms in the liquid phase of the bioreactor, combined with a high protein content in a continuous stable manner is a challenge without making the process economically unattractive.

U.S. Pat. No. 9,157,058B2 (WO2013090769A2) describes an apparatus and method for growth and maintenance of microorganisms and/or bioprocesses using one or more gases as electron donors, electron acceptors, carbon sources, or other nutrients, and for a bioprocess that converts hydrogen and carbon dioxide, or syngas, or producer gas into lipid products, bio-based oils, or other biochemical products. However, it does not disclose optimal conditions for growth and maintenance of the microorganisms nor does it disclose a process to optimize their protein production capacity.

U.S. Pat. No. 9,206,451B2 describes systems and methods for employing chemoautotrophic micro-organisms to capture carbon from industrial waste, but it does not disclose controlled optimal process conditions for growth and maintenance nor a preferred microorganism nor does it disclose a process to optimize their protein production capacity.

Patent application WO2018144965A1 describes microorganisms and bioprocesses that convert gaseous substrates, such as renewable hydrogen and waste carbon dioxide producer gas, or syngas into high-protein biomass. However, it does not disclose controlled optimal process conditions for growth and maintenance of the microorganisms nor does it disclose a process to optimize their protein production capacity.

Patent application WO2019010116A1 describes a method for producing multi-carbon compounds from simple gas feedstocks, such as carbon dioxide, hydrogen and oxygen, by cultivating a consortium of microbial cells specially selected for this purpose in an aqueous culture medium. However, it does not disclose controlled optimal process conditions for growth and maintenance of the microorganisms, nor does it disclose a process to optimize their protein production capacity.

T G Volova and V A Barashkov; in: "Characteristics of Proteins Synthesized by Hydrogen-Oxidizing Microorganisms"; Applied Biochemistry and Microbiology, 2010, describe a process wherein hydrogen-oxidizing bacteria are cultivated to generate a biomass with a 64 to 76% dry weight protein content, but the amounts of carbon dioxide, hydrogen and oxygen used are not disclosed nor does it disclose a process to optimize productivity.

Patent application US2010120104A1 discloses a multi-step method for producing biomass by capturing carbon via obligate and/or facultative chemoautotrophic microorganisms, and/or cell extracts containing enzymes from chemoautotrophic microorganisms. A multitude of different electron donors and acceptors and microorganisms for use in the method are disclosed and no specific process parameters are described.

Patent application WO2011139804A2 discloses a method for producing biomass by capturing carbon with one carbon atom by oxyhydrogen microorganisms and a suitable bioreactor utilizing hydrogen and oxygen gas, wherein the volume of gas occupies at least about 2% of the total volume of the column in which the volume is positioned. No specific process parameters are described for optimization of protein production capacity.

Patent application WO2017165244A1 discloses a method for producing biomass by the capture and conversion of inorganic and/or organic molecules containing only one carbon atom by chemoautotrophic microorganisms. It is disclosed that *Cupriavidus necator* was grown on $H_2$ and $CO_2$ in standard off-the-shelf lab-scale bioreactors to dry biomass densities above 40 g/liter over 6 days. It is also disclosed that *Cupriavidus necator* strains DSM 531 and DSM 541 grown in liquid MSM media with an unspecified Knallgas mixture as the sole carbon and energy source accumulated over 70% and over 80% total protein by weight, respectively, for samples taken during the arithmetic growth phase. However, it is disclosed that *Cupriavidus necator* is grown under oxygen-limiting conditions, which is non-optimal for production of biomass with high protein concentrations at a high, industrial rate. Moreover, the disclosed system used for growing *Cupriavidus necator* is a continuous-fed-batch system, wherein the specific growth rate is a function of gas transfer rates that are not disclosed. Therefore, WO2017165244A1 does not disclose that biomass can be produced at a high rate, wherein the biomass comprises a high protein content, nor are the amounts of carbon dioxide, hydrogen and oxygen used disclosed for obtaining a biomass with a high protein content and/or high biomass production rate.

Morinaga et al. in "Growth Characteristics and Cell Composition of *Alcaligenes eutrophus* in Chemostat Culture"; Agric. Biol. Chem., 1977, describe conditions for culturing *Alcaligenes eutrophus*, but they do not disclose how to achieve the production of biomass at a rate greater than about 7.2 g/l/d and together with a protein content greater than 65% nor do they disclose a growth medium capable of supporting a high concentration of microorganisms. Thus, combining a high productivity with a high density of microorganisms is a challenge.

Thus, there remains a need to identify a set of chemoautotrophic microorganisms that can grow in novel or conventional, controllable, and scalable contained reaction vessels, and that produce protein and other nutritionally beneficial products in a stable and commercially viable manner with high rates of productivity. The growth and maintenance of these microorganisms are then managed by controlled optimal process conditions to fine tune the metabolic and physiological profiles of the microorganisms, ultimately resulting in a high production of a high-quality biomass with a high protein content, preferably by maintaining a high concentration of the microorganisms in the liquid phase of the bioreactor.

SUMMARY OF THE INVENTION

The present invention provides a commercially viable method for producing a high-quality biomass containing a high protein content with a high productivity. This is achieved by using an input stream comprising a gaseous carbon and energy source managed by controlled optimal process conditions, a nutrient supply managed by controlled optimal process conditions and a culture of chemoautotrophic hydrogen oxidising microorganisms. This solution reduces and optimises substrate limitations and enables higher oxygen utilisation, and thereby improved productivity, preferably in a manner which maintains safe operating conditions within the bioreactor, which may be achieved through mitigation of potentially explosive gas mixtures.

The object of the present invention is therefore to provide a method for producing a biomass comprising at least 65% protein of total biomass by dry weight from hydrogen-oxidising microorganisms using one or more input streams comprising one or more gaseous substrates, comprising hydrogen and/or oxygen and/or carbon dioxide, comprising contacting the microorganisms in a liquid phase with a nutrient composition comprising carbon and/or nitrogen and/or phosphorous comprising compounds and the gaseous substrates wherein the input stream and nutrient composition are controlled and wherein the biomass is produced at a rate of more than 10 g/l/d.

It is a further object to provide a method, wherein controlling the input stream comprises maintaining a molar ratio of dissolved hydrogen:oxygen:carbon dioxide of from 0 to 12.748:0 to 4.25:0 to 2.0 in the liquid phase within a distance of from 0 to 500 mm, preferably of from 0 to 100 mm, from a gaseous phase, which is in direct contact with the liquid phase.

It is yet a further object to provide a method of producing biomass from bacteria selected from the genus *Alcaligines* sp.

It is yet a further object to provide a method of producing biomass from bacteria selected from the genus *Cupriavidus* sp.

In a further aspect, the invention provides a method of isolating the produced biomass and removing the nutrient composition, comprising downstream processing.

It is a further object to provide a method of isolating the produced biomass by removing the nutrient composition, comprising dewatering and/or drying the biomass such that the biomass comprises a water content of less than 5% by weight.

It is yet a further object to provide a biomass comprising protein comprising an amino acid content comprising a histidine content of from 0.9 to 4.8% of total biomass dry weight protein content, an isoleucine content of from 2.0 to 6.9% of total biomass dry weight protein content, a leucine content of from 3.8 to 12.0% of total biomass dry weight protein content, a lysine content of from 3.0 to 11.1% of total biomass dry weight protein content, a methionine content of from 1.1 to 5.4% of total biomass dry weight protein content, a phenylalanine content of from 1.7 to 8.5% of total biomass dry weight protein content, a threonine content of from 1.6 to 6.9% of total biomass dry weight protein content, a tryptophan content of from 0.4 to 3.9% of total biomass dry weight protein content, and a valine content of from 1.7 to 9.3% of total biomass dry weight protein content.

In a further aspect, the invention provides a biomass comprising a lipid content of from 2.3 to 18% of total biomass dry weight comprising a fatty acid content comprising a C16:0 palmitic acid content of from 23 to 60% of total biomass dry weight fatty acid content, a C16:1 palmitoleic acid content of from 3.8 to 22.3% of total biomass dry weight fatty acid content, and a C17:1 heptadecenoic acid content of from 23 to 60% of total biomass dry weight fatty acid content.

It is yet a further object to provide a use of the nutrient composition obtained by a method of isolating the produced biomass as a nutrient composition for producing biomass.

Another object of the present invention is to provide a use of the biomass, wherein the biomass is used to feed or provide nutrition to one or more organisms.

SHORT DESCRIPTION OF THE FIGURES

FIG. 1 discloses a preferred embodiment of a system for operating the method.

Figure 8:
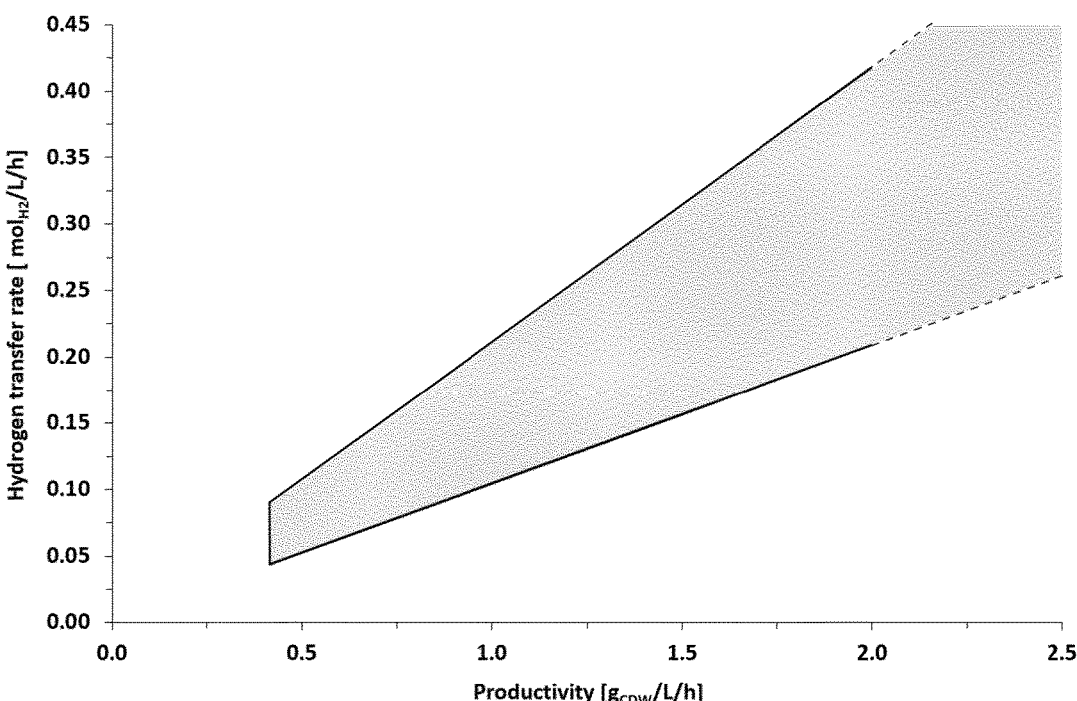
FIG. 8A shows a projection of preferred hydrogen transfer rates in relation to biomass production rate produced according to the invention.
Figure 8:
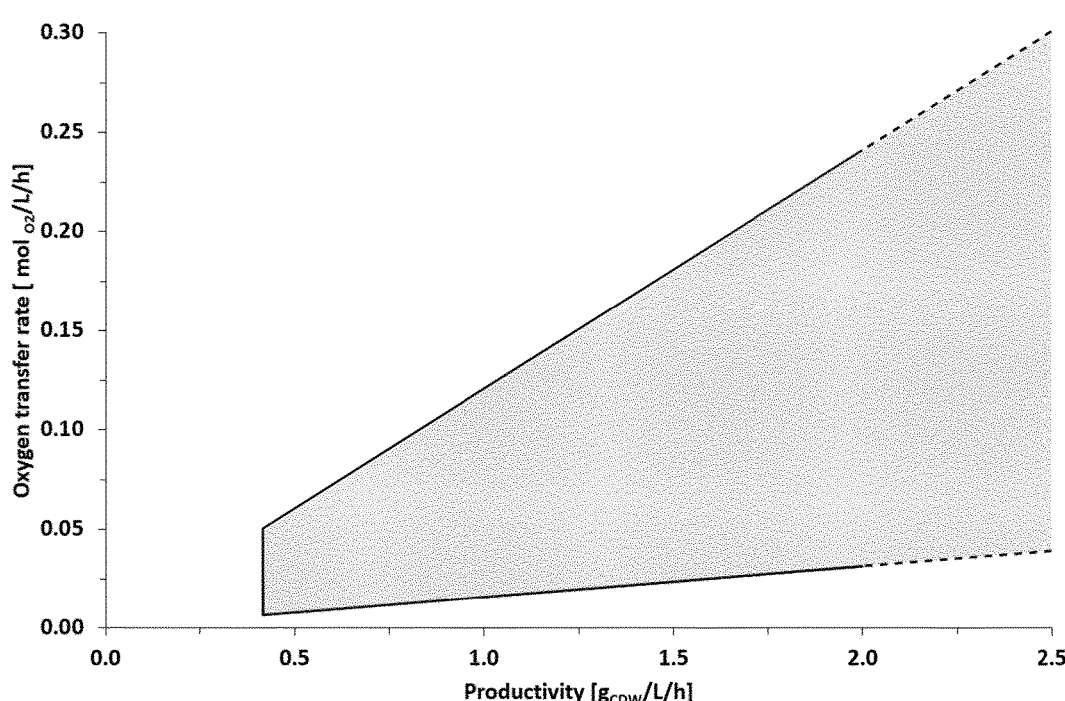

FIG. 8 B shows a projection of preferred oxygen transfer rates in relation to biomass production rate produced according to the invention.

The following list comprises definitions of reference numerals as employed in the figures:

1 Oxygen/air input
2 Hydrogen input
3 Carbon dioxide input
4 Inorganic nitrogen (e.g. urea) addition
5 pH buffer addition
6 Liquid growth media addition
7 Unutilised gas recycling
8 Removal of liquid containing biomass
9 Downstream processing steps
10 Liquid recycling
11 Optional downstream processing steps

DETAILED DESCRIPTION OF THE INVENTION

Definitions

Biomass herein is understood to mean the total weight of microorganisms and their progeny, products and/or metabolites.

Bioreactor is understood herein as to be a system for maintaining and/or growing microorganisms comprising a gaseous phase, commonly called the headspace, and a liquid phase. The microorganisms are grown and maintained in the liquid phase.

Hydrogen-oxidising microorganisms are meant to be understood to comprise facultative chemoautotrophic bacteria that can use hydrogen as electron donor. The group of aerobic hydrogen-oxidizing bacteria, also known as Knallgas-bacteria, is physiologically defined and comprises bacteria from different taxonomic units. This group is defined by the ability to use gaseous hydrogen as electron donor with oxygen as electron acceptor and to fix carbon dioxide.

Input stream is herein understood to mean a supply of nutrients and/or energy for growth and/or maintenance of microorganisms comprising a liquid phase and/or a gaseous phase.

Liquid phase herein is understood to mean a volume comprising liquid material. In the liquid phase microorganisms are commonly grown and maintained. Biomass mostly subsists within the liquid phase. The liquid phase can also comprise solid material functioning as growth and maintenance substrates for microorganisms to attach to.

The liquid phase may comprise carbon, nitrogen and/or phosphorous-comprising compounds, wherein carbon-comprising compounds may be formate or methanol, but preferably are understood to be essentially limited to dissolved $CO_2$, or urea, wherein the latter may also be considered a bioavailable $N_2$ source. Formate or methanol can be converted to $CO_2$ in the liquid phase of the bioreactor, which can for example be catalysed by enzymes present inside or outside microorganisms, thereby indirectly acting as a supply of a gaseous substrate.

Gaseous phase is understood herein to mean a volume consisting of gaseous material and in contact with a liquid phase. The gaseous phase in a bioreactor is commonly called the headspace and is typically located directly above the liquid phase. To clarify, gas or gaseous substrate sparged into the liquid phase is not the gaseous phase, but becomes part of the gaseous phase upon exiting the liquid phase.

Gaseous substrate is understood to mean a gaseous supply of nutrients and/or energy for growth and/or maintenance of microorganisms.

Cement kiln is understood to mean a space used for the pyro-processing stage of manufacture of Portland and other types of hydraulic cement, in which calcium carbonate reacts with silica-bearing minerals to form a mixture of calcium silicates.

Syngas, or synthesis gas, is herein understood to mean a mixture comprising carbon monoxide, carbon dioxide and hydrogen. Syngas is produced by gasification of a carbon containing fuel to a gaseous product. The exact chemical composition of syngas varies based on the raw materials and the processes. One of the uses of syngas is as a fuel to manufacture steam or electricity. Another use is as a basic chemical building block for many petrochemical and refining processes. Syngas can be produced from many sources, including natural gas, coal, petroleum-based materials, biomass, other materials that would be rejected as waste, or virtually any hydrocarbon feedstock.

"Knallgas" is understood to mean a mixture of hydrogen and oxygen gases, which is highly combustible. A molar ratio of 2:1 is sufficient for maximum ignition efficiency.

Sparging is understood to mean a process in which a gas is bubbled through a liquid.

Dry weight or dry matter of a material herein is understood to mean the material consisting of all its constituents, but essentially excluding water. Examples of obtaining the dry weight or dry matter of a material are using centrifugation, drum drying, belt drying, evaporation, freeze drying, heating, spray drying, vacuum drying and/or vacuum filtration such that the water content of the material is removed.

Downstream processing is understood to mean one or more processing steps applied to a liquid phase removed from a bioreactor, which may include a kill-step process, a dewatering process, or a drying process.

Kill-step is understood to mean a process that achieves the reproductive inactivation of microorganisms. This process may occur within the liquid phase, a dewatered liquid phase, or dried biomass, for example by using an ultra-high-pressure homogeniser, acid, base, solvent, or heat-based microbial killing methods.

Dewatering is understood herein to mean a first process of removing liquid and/or a nutrient composition from biomass or a composition comprising biomass. Examples of dewatering are centrifugation, evaporation, heating, tangential flow filtration, and vacuum filtration. Dewatering may be followed by further downstream processing.

Drying is understood to mean a process of removing water from biomass or a composition comprising biomass to produce a biomass consisting of all its constituents, but essentially excluding water. Examples of drying are drum drying, belt drying, freeze drying, spray drying and vacuum drying.

Purifying carbon dioxide derived from the exhaust gas of a production or combustion process is understood to mean obtaining a volume consisting of essentially only carbon dioxide wherein other elements of the exhaust gas are substantially removed by devices and methods known in the art such as for example by using electrostatic precipitators or baghouses to remove ash and other particulates, using denitrification units to remove nitrogen oxides, using wet scrubbers, spray-dry scrubbers or dry sorbent injection systems to remove sulfur oxides. Carbon dioxide can be captured in post-combustion processes by separation methods known in the art, for example by using a solvent such as an amine to form a carbonate salt. The carbon dioxide is absorbed by the solvent after which it can be released by heat to form a highly purified stream of carbon dioxide.

Bioavailable nitrogen is understood to mean all nitrogen species that are readily available for uptake by microorganisms, including for example urea, ammonia, and amino-acids. For clarity, this is excluding dinitrogen ($N_2$).

Process limiting is understood to mean an instance where a substance can be measured as zero or close to zero in the liquid phase.

Chemostat is understood to mean a bioreactor in which the chemical environment is maintained in a more or less steady state with respect to for example microorganism concentration, pH, (dissolved) gaseous substrates, nutrient composition, liquid phase volume and other parameters known to a person skilled in the art.

DETAILED DESCRIPTION OF THE INVENTION

The present invention is directed to a process for producing biomass containing at least 65% protein content by dry weight with hydrogen-oxidizing bacteria grown within a bioreactor with economically favourable substrate conversion yields and—and with a high productivity, preferably with a high operating microorganism concentration within the process. To this end, relevant background process conditions and control parameters have been established for continuous fermentation with hydrogen-oxidizing bacteria. Appropriately controlling the availability of growth substrates (gases, inorganic nitrogen or phosphate), can improve the overall biomass productivity of gas-fermentation systems while simultaneously optimizing the protein concentration within the produced biomass thereby generating an optimal biomass.

A multitude of potential sources of gaseous carbon and energy exist, which may be used to grow chemoautotrophic microorganisms for use in human and animal nutritional products and other chemicals. Sources include but are not limited to industrial off-gas, industrial flue-gas, and industrial product-gas, as well as direct-air capture gas, and in-situ electrochemical production gas. Chemoautotrophic metabolism herein refers to a metabolic mode in which the microorganism takes up inorganic carbon, such as by capturing carbon dioxide or formate or methanol, as a primary carbon source, and obtains energy from a chemical source, such as by oxidizing hydrogen. By converting inorganic carbon to organic carbon these microbes serve as primary producers in natural environments. Many of these chemoautotrophic microbes can be cultured on direct or indirect gas feedstocks in bioreactors for commercial production of biomass, which can be processed into nutritional products such as animal feed, companion animal feed, or even food for humans.

Preferably, the microorganisms are fed by an indirect industrial waste gas feedstock which has been purified, filtered and/or concentrated. Besides the desired gaseous substrates for microbial growth industrial waste gas contains other elements which can reduce the growth of the microbes and/or quality of the produced biomass.

Accordingly, the method of the present invention is a method for producing a biomass comprising at least 65% protein of total biomass by dry weight from hydrogen-oxidising microorganisms using one or more input streams comprising one or more gaseous substrates, comprising hydrogen and/or oxygen and/or carbon dioxide, comprising contacting the microorganisms in a liquid phase with a nutrient composition comprising carbon and/or nitrogen and/or phosphorous-comprising compounds and the gaseous substrates wherein the input stream and nutrient composition are controlled and wherein the biomass is produced at a rate of more than 10 g/l/d.

The biomass according to the invention comprises the cell mass of the microorganisms and/or their products, preferably the biomass is the cell mass of the microorganisms and/or their products, more preferably the biomass is the cell mass of the microorganisms.

According to the method of invention, most preferably the one or more gaseous substrates comprises hydrogen and oxygen and carbon dioxide. Preferably, the one or more gaseous substrates comprises hydrogen and oxygen. Preferably, the one or more gaseous substrates comprises hydrogen and carbon dioxide. Preferably, the one or more gaseous substrates comprises oxygen and carbon dioxide. Preferably, the one or more gaseous substrates comprises hydrogen. Preferably, the one or more gaseous substrates comprises oxygen. Preferably, the one or more gaseous substrates comprises carbon dioxide.

According to the method of invention, most preferably the nutrient composition comprises carbon-comprising compounds and nitrogen-comprising-compounds and phosphorous-comprising compounds. Preferably, the nutrient composition comprises carbon-comprising compounds and nitrogen-comprising-compounds. Preferably the nutrient composition comprises carbon-comprising compounds and phosphorous-comprising compounds. Preferably, the nutrient composition comprises nitrogen-comprising-compounds and phosphorous-comprising compounds. Preferably, the nutrient composition comprises carbon-comprising compounds. Preferably, the nutrient composition comprises nitrogen-comprising-compounds. Preferably, the nutrient composition comprises phosphorous-comprising compounds.

Thus, an embodiment of a method according to the invention is a method for producing a biomass comprising at least 65% protein of total biomass by dry weight from hydrogen-oxidising microorganisms using one or more input streams comprising one or more gaseous substrates, comprising hydrogen and oxygen, comprising contacting the microorganisms in a liquid phase with a nutrient composition comprising nitrogen and phosphorous-comprising compounds and the gaseous substrates, wherein the one or more gaseous substrates comprises carbon dioxide and/or the nutrient composition comprises carbon-comprising compounds, wherein the input stream and nutrient composition are controlled and wherein the biomass is produced at a rate of more than 10 g/l/d.

The biomass produced by the method of the present invention is produced at a rate of more than 10 g/l/d. Preferably, of more than 10.5, 11.0, 11.5, 12.0, 12.5, 13.0, 13.5, 14.0, 14.5, 15.0, 15.5, 16.0, 16.5, 17.0, 17.5, 18.0, 18.5, 19.0, 19.5 or 20.0 g/l/d. Preferably, the biomass is produced at a rate of from 10.0 to 100 g/l/d, from 10.0 to 90 g/l/d, from 10.0 to 80 g/l/d, from 10.0 to 50 g/l/d, from 10.5 to 100 g/l/d, from 10.5 to 90 g/l/d, from 10.5 to 80 g/l/d, from 10.5 to 50 g/l/d, from 11.0 to 100 g/l/d, from 11.0 to 90 g/l/d, from 11.0 to 80 g/l/d, from 11.0 to 50 g/l/d, from 11.5 to 100 g/l/d, from 11.5 to 90 g/l/d, from 11.5 to 80 g/l/d, from 11.5 to 50 g/l/d, from 12.0 to 100 g/l/d, from 12.0 to 90 g/l/d, from 12.0 to 80 g/l/d, from 12.0 to 50 g/l/d, from 12.5 to 100 g/l/d, from 12.5 to 90 g/l/d, from 12.5 to 80 g/l/d, from 12.5 to 50 g/l/d, from 13.0 to 100 g/l/d, from 13.0 to 90 g/l/d, from 13.0 to 80 g/l/d, from 13.5 to 50 g/l/d, from 13.5 to 100 g/l/d, from 13.5 to 90 g/l/d, from 13.5 to 80 g/l/d, from 13.5 to 50 g/l/d, from 14.0 to 100 g/l/d, from 14.0 to 90 g/l/d, from 14.0 to 80 g/l/d, from 14.0 to 50 g/l/d, from 14.5 to 100 g/l/d, from 14.5 to 90 g/l/d, from 14.5 to 80 g/l/d, from 14.5 to 50 g/l/d, from 15.0 to 100 g/l/d, from 15.0 to 90 g/l/d, from 15.0 to 80 g/l/d, from 15.0 to 50 g/l/d, from 15.5 to 100 g/l/d, from 15.5 to 90 g/l/d, from 15.5 to 80 g/l/d, from 15.5 to 50 g/l/d, from 16.0 to 100 g/l/d, from 16.0 to 90 g/l/d, from 16.0 to 80 g/l/d, from 16.0 to 50 g/l/d, from 16.5 to 100 g/l/d, from 16.5 to 90 g/l/d, from 16.5 to 80 g/l/d, from 16.5 to 50 g/l/d, from 17.0 to 100 g/l/d, from 17.0 to 90 g/l/d, from 17.0 to 80 g/l/d, from 17.0 to 50 g/l/d, from 18.0 to 100 g/l/d, from 18.0 to 90 g/l/d, from 18.0 to 80 g/l/d, from 18.0 to 50 g/l/d, from 19.0 to 100 g/l/d, from 19.0 to 90 g/l/d, from 19.0 to 80 g/l/d, from 19.0 to 50 g/l/d, from 20.0 to 100 g/l/d, from 20.0 to 90 g/l/d, from 20.0 to 80 g/l/d, or from 20.0 to 50 g/l/d.

In addition, using highly concentrated sources of gaseous substrates reduces the volume of other non-substrate gases in the environment of the microorganisms, thereby improving the efficiency of the added gaseous substrates and also enabling an improved control over the amounts of gaseous substrates in the environment of the microorganisms. The gaseous substrates may be added to the liquid phase individually or as any premixed combination. According to the invention, the gaseous substrates are preferably added with as low as possible concentrations of non-substrate gases such as nitrogen or carbon monoxide. Adding one or more gaseous substrates to the liquid phase comprises contacting the gaseous substrate with the liquid phase such that the gaseous substrate mixes with at least a portion of the liquid phase. When a ratio of one or more gaseous substrates is added to the liquid phase a person skilled in the art understands that the one or more gaseous substrates may be added simultaneously or subsequently.

Preferably, a concentrated gaseous substrate has a concentration of from 2 to 100% (v/v), from 5 to 100% (v/v), from 10 to 100% (v/v), from 20 to 100% (v/v), from 30 to 100% (v/v), from 40 to 100% (v/v), from 50 to 100% (v/v), from 60 to 100% (v/v), from 70 to 100% (v/v), from 80 to 100% (v/v), from 90 to 100% (v/v), from 95 to 100% (v/v), from 98 to 100% (v/v), from 99 to 100% (v/v), from 2 to 90% (v/v), from 5 to 90% (v/v), from 10 to 90% (v/v), from 20 to 90% (v/v), from 30 to 90% (v/v), from 40 to 90% (v/v), from 50 to 90% (v/v), from 60 to 90% (v/v), from 70 to 90% (v/v), from 80 to 90% (v/v), from 2 to 80% (v/v), from 5 to 80% (v/v), from 10 to 80% (v/v), from 20 to 80% (v/v), from 30 to 80% (v/v), from 40 to 80% (v/v), from 50 to 80% (v/v), from 60 to 80% (v/v), from 70 to 80% (v/v), from 2 to 70% (v/v), from 5 to 70% (v/v), from 10 to 70% (v/v), from 20 to 70% (v/v), from 30 to 70% (v/v), from 40 to 70% (v/v), from 50 to 70% (v/v), from 60 to 70% (v/v), from 2 to 60% (v/v), from 5 to 60% (v/v), from 10 to 60% (v/v), from 20 to 60% (v/v), from 30 to 60% (v/v), from 40 to 60% (v/v), from 50 to 60% (v/v), from 2 to 50% (v/v), from 5 to 50% (v/v), from 10 to 50% (v/v), from 20 to 50% (v/v), from 30 to 50% (v/v), from 40 to 50% (v/v), from 2 to 40% (v/v), from 5 to 40% (v/v), from 10 to 40% (v/v), from 20 to 40% (v/v), from 30 to 40% (v/v), from 2 to 30% (v/v), from 5 to 30% (v/v), from 10 to 30% (v/v), from 20 to 30% (v/v), from 2 to 20% (v/v), from 5 to 20% (v/v), from 10 to 20% (v/v), from 2 to 10% (v/v), from 5 to 10% (v/v), or from 2 to 5% (v/v).

Using highly concentrated sources of gaseous substrates reduces the volume of other non-substrate gases in the environment of the microorganisms thereby ideally resulting in the gaseous phase consisting only of hydrogen, oxygen and carbon dioxide. Thus, herein is also provided the method of the present invention, wherein the gaseous phase consists essentially only of the hydrogen, oxygen and carbon dioxide.

Preferably, the input stream is controlled by adding hydrogen in a concentration of from 10 to 100% (v/v), oxygen in a concentration of from 2 to 100% (v/v) and carbon dioxide in a concentration of from 2 to 100% (v/v) to the liquid phase, individually or as any premixed combination thereof. More preferably, the input stream is controlled by adding hydrogen in a concentration of from 80 to 100% (v/v), oxygen in a concentration of from 20 to 100% (v/v) and carbon dioxide in a concentration of from 5 to 100% (v/v) to the liquid phase, individually or as any premixed combination thereof. More preferably, the input stream is controlled by adding to the liquid phase, individually or as any premixed combination thereof, hydrogen in a concentration of from 20 to 100% (v/v), from 30 to 100% (v/v), from 40 to 100% (v/v), from 50 to 100% (v/v), from 60 to 100% (v/v), from 70 to 100% (v/v), from 80 to 100% (v/v), from 90 to 100% (v/v), from 95 to 100% (v/v), from 10 to 90% (v/v), from 20 to 90% (v/v), from 30 to 90% (v/v), from 40 to 90% (v/v), from 50 to 90% (v/v), from 60 to 90% (v/v), from 70 to 90% (v/v), from 80 to 90% (v/v), from 10 to 80% (v/v), from 20 to 80% (v/v), from 30 to 80% (v/v), from 40 to 80% (v/v), from 50 to 80% (v/v), from 60 to 80% (v/v) or from 70 to 80% (v/v), oxygen in a concentration of from 2 to 100% (v/v),), from 5 to 100% (v/v), from 10 to 100% (v/v), from 20 to 100% (v/v), from 30 to 100% (v/v), from 40 to 100% (v/v), from 50 to 100% (v/v), from 60 to 100% (v/v), from 70 to 100% (v/v), from 80 to 100% (v/v), from 90 to 100% (v/v), from 95 to 100% (v/v), from 2 to 90% (v/v), from 5 to 90% (v/v), from 10 to 90% (v/v), from 20 to 90% (v/v), from 30 to 90% (v/v), from 40 to 90% (v/v), from 50 to 90% (v/v), from 60 to 90% (v/v), from 70 to 90% (v/v), from 80 to 90% (v/v), from 2 to 80% (v/v), from 5 to 80% (v/v), from 10 to 80% (v/v), from 20 to 80% (v/v), from 30 to 80% (v/v), from 40 to 80% (v/v), from 50 to 80% (v/v), from 60 to 80% (v/v), from 70 to 80% (v/v), from 2 to 70%

(v/v), from 5 to 70% (v/v), from 10 to 70% (v/v), from 20 to 70% (v/v), from 30 to 70% (v/v), from 40 to 70% (v/v), from 50 to 70% (v/v), from 60 to 70% (v/v), from 2 to 60% (v/v), from 5 to 60% (v/v), from 10 to 60% (v/v), from 20 to 60% (v/v), from 30 to 60% (v/v), from 40 to 60% (v/v), from 50 to 60% (v/v), from 2 to 50% (v/v), from 5 to 50% (v/v), from 10 to 50% (v/v), from 20 to 50% (v/v), from 30 to 50% (v/v), from 40 to 50% (v/v), from 2 to 40% (v/v), from 5 to 40% (v/v), from 10 to 40% (v/v), from 20 to 40% (v/v), from 30 to 40% (v/v), from 2 to 30% (v/v), from 5 to 30% (v/v), from 10 to 30% (v/v), from 20 to 30% (v/v), from 2 to 20% (v/v), from 5 to 20% (v/v), from 10 to 20% (v/v), from 2 to 10% (v/v), from 5 to 10% (v/v), or from 2 to 5% (v/v) and carbon dioxide in a concentration of from 2 to 100% (v/v), from 5 to 100% (v/v), from 10 to 100% (v/v), from 20 to 100% (v/v), from 30 to 100% (v/v), from 40 to 100% (v/v), from 50 to 100% (v/v), from 60 to 100% (v/v), from 70 to 100% (v/v), from 80 to 100% (v/v), from 90 to 100% (v/v), from 95 to 100% (v/v), from 2 to 90% (v/v), from 5 to 90% (v/v), from 10 to 90% (v/v), from 20 to 90% (v/v), from 30 to 90% (v/v), from 40 to 90% (v/v), from 50 to 90% (v/v), from 60 to 90% (v/v), from 70 to 90% (v/v), from 80 to 90% (v/v), from 2 to 80% (v/v), from 5 to 80% (v/v), from 10 to 80% (v/v), from 20 to 80% (v/v), from 30 to 80% (v/v), from 40 to 80% (v/v), from 50 to 80% (v/v), from 60 to 80% (v/v), from 70 to 80% (v/v), from 2 to 70% (v/v), from 5 to 70% (v/v), from 10 to 70% (v/v), from 20 to 70% (v/v), from 30 to 70% (v/v), from 40 to 70% (v/v), from 50 to 70% (v/v), from 60 to 70% (v/v), from 2 to 60% (v/v), from 5 to 60% (v/v), from 10 to 60% (v/v), from 20 to 60% (v/v), from 30 to 60% (v/v), from 40 to 60% (v/v), from 50 to 60% (v/v), from 2 to 50% (v/v), from 5 to 50% (v/v), from 10 to 50% (v/v), from 20 to 50% (v/v), from 30 to 50% (v/v), from 40 to 50% (v/v), from 2 to 40% (v/v), from 5 to 40% (v/v), from 10 to 40% (v/v), from 20 to 40% (v/v), from 30 to 40% (v/v), from 2 to 30% (v/v), from 5 to 30% (v/v), from 10 to 30% (v/v), from 20 to 30% (v/v), from 2 to 20% (v/v), from 5 to 20% (v/v), from 10 to 20% (v/v), from 2 to 10% (v/v), from 5 to 10% (v/v), or from 2 to 5% (v/v). Even more preferably, the input stream is controlled by adding hydrogen in a concentration of from 70 to 100% (v/v), oxygen in a concentration of from 20 to 100% (v/v) and carbon dioxide in a concentration of from 5 to 100% (v/v) to the liquid phase, individually or as any premixed combination thereof.

Substrate gases are preferably added with as low as possible concentrations of non-substrate gases such as nitrogen or carbon monoxide.

Advantageously, the microorganisms are fed by an indirect industrial waste gas feedstock which has been purified, filtered and/or concentrated. Preferably, the gaseous substrate is derived from the exhaust gas of a production or combustion process. More preferably, the hydrogen is derived from the exhaust gas of a production or combustion process. Even more preferably, the carbon dioxide is derived from the exhaust gas of a production or combustion process.

Preferably, the carbon dioxide derived from the exhaust gas of a production or combustion process is purified and concentrated to a concentration of from 20 to 100% (v/v). More preferably, the carbon dioxide is purified and concentrated to a concentration of from 30 to 100% (v/v), from 40 to 100% (v/v), from 50 to 100% (v/v), from 60 to 100% (v/v), from 70 to 100% (v/v), from 80 to 100% (v/v), from 90 to 100% (v/v), from 95 to 100% (v/v), from 99 to 100% (v/v), from 20 to 90% (v/v), from 30 to 90% (v/v), from 40 to 90% (v/v), from 50 to 90% (v/v), from 60 to 90% (v/v), from 70 to 90% (v/v), from 80 to 90% (v/v), from 20 to 80%

(v/v), from 30 to 80% (v/v), from 40 to 80% (v/v), from 50 to 80% (v/v), from 60 to 80% (v/v), from 70 to 80% (v/v), from 20 to 70% (v/v), from 30 to 70% (v/v), from 40 to 70% (v/v), from 50 to 70% (v/v), from 60 to 70% (v/v), from 20 to 60% (v/v), from 30 to 60% (v/v), from 40 to 60% (v/v), from 50 to 60% (v/v), from 20 to 50% (v/v), from 30 to 50% (v/v), from 40 to 50% (v/v), from 20 to 40% (v/v), from 30 to 40% (v/v), or from 20 to 30% (v/v).

Chemoautotrophic metabolism is mainly found in a number of bacteria, including, but not limited to purple non-sulfur bacteria such as *Rhodobacter capsulatus, Rhodobacter sphaeroides, Rhodpsuedamonas palustris*, the pseudomonas, such as *Pseudomonas carboxydovorans*, the aquificales bacteria, such as *Hydrogenobacter thermophilus*, the methanogenous bacteria, such as *Methanobacterium thermoautotrophicum*, the alphaproteobacteria, such as *Xanthobacter flavus*, the betaproteobacteria, such as *Ralstonia metallidurans, Cupriavidus necator*, the gammaproteobacteria, such as *Hydrogenovibrio marinus*, the epsilonproteobacteria, such as *Helicobacter pylori*, the acetogenous bacteria, such as *Acetobacterium woodii*, or other microbes which express an uptake hydrogenase and a carbon dioxide fixation metabolism, whether endogenous or introduced through genetic manipulation, mutation, selection or directed evolution. Most of these microbes are capable of heterotrophic as well as phototrophic metabolism, or mixed metabolism using both sources of energy and carbon. Hydrogen is used as the energy source and carbon dioxide is used as the carbon source. Carbon monoxide can also act as an energy source and a carbon source.

Preferably, the microorganisms according to the method of the invention comprise bacteria selected from: *Rhodopseudomonas* sp.; *Rhodospirillum* sp.; *Rhodococcus* sp.; *Rhodobacter* sp.; *Rhizobium* sp.; *Thiocapsa* sp.; *Pseudomonas* sp.; *Nocardia* sp.; *Hydrogenomas* sp.; *Hydrogenobacter* sp.; *Hydrogenovibrio* sp.; *Helicobacter* sp.; *Xanthobacter* sp.; *Hydrogenophaga* sp.; *Bradyrhizobium* sp.; *Ralstonia* sp.; *Gordonia* sp.; *Mycobacteria* sp.; *Alcaligenes* sp.; *Cupriavidus* sp.; *Variovorax* sp.; *Acidovorax* sp.; *Anabaena* sp.; *Scenedesmus* sp.; *Chlamydomonas* sp.; *Ankistrodesmus* sp.; *Rhaphidium* sp. or *Arthrobacter* sp., and combinations thereof. More preferably, the microorganisms comprise bacteria selected from the genus *Alcaligenes* sp. or *Cupriavidus* sp. More preferably, the microorganisms comprise bacteria selected from the genus *Alcaligenes* sp. More preferably, the microorganisms comprise bacteria selected from the genus *Cupriavidus* sp. Even more preferably, the microorganisms comprise bacteria selected from the species *Cupriavidus necator*.

The properties of biomass produced by chemoautotrophic bacteria directly relate to its value for certain applications. For example, for animal feed and food applications, protein content and amino acid composition are essential for nutritional quality.

The ratios of protein, lipid, DNA, RNA, and other components of cellular biomass are mediated by growth conditions, growth rate, and the carbon-nitrogen ratio. Control of substrate availability and general process conditions therefore directly affect the amount and quality of the biomass produced during fermentation processes. Maximal baseline productivity requires the avoidance of substrate limitation, however as microbial densities increase within a fermentation the rate of substrate utilisation exceeds the supply, particularly in the context of gaseous substrates. This means that high gas flow rates are required to establish and maximize productivity. However, achieving this is challenging in the context of explosive gas mixtures containing hydrogen and oxygen. Hydrogen and oxygen containing gas mixtures produce an explosive mixture when combined at ratios containing both more than 5% oxygen and more than 4% hydrogen, as for instance disclosed in R K Kumar; FLAM-MABILITY LIMITS OF HYDROGEN-OXYGEN-DI-LUENT MIXTURES; Journal of Fire Sciences, 1985.

In the present method, oxygen and hydrogen gas inputs are controlled as part of a feedback loop to allow for initial addition of the gas to the system above the explosive limit, as it is injected initially into the liquid media phase. The feedback control then ensures that oxygen and/or hydrogen is being sufficiently utilised by the system such that the gas resulting in the headspace can remain below explosive safety limits, of 5% (v/v) for oxygen and 4% (v/v) for hydrogen under standard conditions. Additionally, all three gas inputs are controlled such that oxygen or hydrogen is maintained as the limiting gas within the system.

Combining these gas controls with defined parameters for background conditions, media compositions, inorganic nitrogen addition, and dilution rate, advantageously enables modulation of biomass composition through the direct metabolic and physiological limitations imposed on the microbes. Ammonium hydroxide and/or other bioavailable nitrogen sources are supplied to the process, directly and/or through incorporation into liquid media input stream and/or recycled liquid streams, such that a minimum of 10 g of atomic nitrogen is provided for every 100 g of biomass produced, controlled as part of a feedback loop in response to the density of the cells in the liquid phase and dilution rate. In addition to the gaseous substrates, hydrogen-oxidizing bacteria require a source of bioavailable nitrogen for production of proteins. This nitrogen is a major contributing factor to protein content, independent of respective molecular associations such as in ammonium hydroxide ($NH_4OH$) or ammonium chloride ($NH_3Cl$). There is no maximum threshold foreseen as excess bioavailable nitrogen in the liquid phase will be recycled.

In order for the microorganisms to produce sufficient protein a sufficient amount of nitrogen, an essential component of amino acids, needs to be supplied. According to the method of the invention, controlling the nutrient composition comprises adding at least 10 g bioavailable nitrogen per 100 g biomass dry weight to be produced and which is present in the liquid phase. Preferably, controlling the nutrient composition comprises adding of from 10.0 to 50000 g bioavailable nitrogen per 100 g biomass dry weight to be produced and which is present in the liquid phase. Preferably, controlling the nutrient composition comprises adding of from 10.5 to 50000 g, 11.0 to 50000 g, 11.5 to 50000 g, 12.0 to 50000 g, 12.5 to 50000 g, from 13.0 to 50000 g, from 13.5 to 50000 g, from 14.0 to 50000 g, from 14.5 to 50000 g, from 15.0 to 50000 g, from 16 to 50000 g, from 17 to 50000 g, from 18 to 50000 g, from 19 to 50000 g, from 20 to 50000 g, from 21 to 50000 g, from 22 to 50000 g, from 23 to 50000 g, from 24 to 50000 g, from 25 to 50000 g, from 26 to 50000 g, from 27 to 50000 g, from 28 to 50000 g, from 29 to 50000 g, from 30 to 50000 g, from 35 to 50000 g, from 40 to 50000 g, from 45 to 50000 g, from 50 to 50000 g, from 60 to 50000 g, from 70 to 50000 g, from 80 to 50000 g, from 90 to 50000 g, from 100 to 50000 g, from 110 to 50000 g, from 120 to 50000 g, from 130 to 50000 g, from 140 to 50000 g, from 150 to 50000 g, from 160 to 50000 g, from 170 to 50000 g, from 180 to 50000 g, from 190 to 50000 g, from 200 to 50000 g, from 250 to 50000 g, from 300 to 50000 g, from 350 to 50000 g, from 400 to 50000 g, from 450 to 50000 g, from 500 to 50000 g, from 1000 to 50000 g, from 1500 to 50000 g, from 2000 to 50000 g, from 2500 to 50000 g, from 3000 to 50000 g, from 3500 to 50000 g, from 4000 to 50000 g, from 4500 to 50000 g, from 5000 to 50000 g, from 6000 to 50000 g, from 7000 to 50000 g, from 8000 to 50000 g, from 9000 to 50000 g, from 10000 to 50000 g, from 15000 to 50000 g, from 20000 to 50000 g, from 25000 to 50000 g or from 30000 to 50000 g bioavailable nitrogen per 100 g biomass dry weight to be produced and which is present in the liquid phase.

According to the invention, controlling the nutrient composition preferably comprises adding a suitable base, such as for example ammonium hydroxide ($NH_4OH$) or NaOH, to the liquid phase in order to maintain the pH of the liquid phase at a physiologically suitable pH. Preferably, the physiologically suitable pH is from 6.0 to 7.5 or 8.0, more preferably the pH is from 6.5 to 7.0.

According to the invention, controlling the nutrient composition preferably comprises adding a growth medium which has a pH of from 1.0 to 3.0 or 4.0 before being added to the liquid phase. Preferably, the growth medium has a pH of from 2.2 to 3.2, or about 2.8. The low pH prevents precipitation of the components of the growth medium when being prepared. The components of the growth medium comprise the components or substantially similar components as the growth medium as disclosed in example 1. The growth medium is prepared as disclosed in example 1.

The liquid phase within the bioreactor is replaced with growth medium and/or other liquid input streams at a rate of between 4 to 80% of the volume per hour in order to maximise the production rate, protein content, and quality of the biomass.

Certain specific rates of replacement of the liquid phase within the bioreactor lead to higher levels of protein content and quality of the biomass. Preferably, the liquid phase of a bioreactor where the microorganisms are grown and maintained is replaced per hour at a volume of from 4 to 10%, from 4 to 20%, from 4 to 30%, from 4 to 40%, from 4 to 50%, from 4 to 60%, from 4 to 70%, from 4 to 80%, from 10 to 20%, from 10 to 30%, from 10 to 40%, from 10 to 50%, from 10 to 60%, from 10 to 70%, from 10 to 80%, from 20 to 30%, from 20 to 40%, from 20 to 50%, from 20 to 60%, from 20 to 70%, from 20 to 80%, from 30 to 40%, from 30 to 50%, from 30 to 60%, from 30 to 70%, from 30 to 80%, from 40 to 50%, from 40 to 60%, from 40 to 70%, from 40 to 80%, from 50 to 60%, from 50 to 70%, from 50 to 80%, from 60 to 70%, from 60 to 80%, or from 70 to 80%. Consumption of the gaseous substrates by the microorganisms in the system is limited by the dissolution rate of the gas into the liquid phase and its distribution throughout the liquid phase. The volumetric mass-transfer coefficient (kLa) represents the dissolution rate or efficiency of translating a concentration gradient of a dissolved gas from its gaseous phase to a liquid phase. In order to obtain a high utilisation of the gaseous substrates and a subsequent high rate of biomass and protein production it is necessary to maintain a kLa as high as possible. Preferably, adding a gaseous substrate to the liquid phase at a concentration as high as possible increases the driving force for dissolution and diffusion of the gas into the bulk liquid phase. Preferably, the gaseous substrate is added at its saturation concentration.

Gaseous substrate ratios, concentrations and consumption by microorganisms need to be maintained by sufficient gas transfer into the liquid phase. Controlling the input stream comprises maintaining hydrogen, oxygen and carbon dioxide at a gas transfer coefficient of from 1 to 5000 h$^{-1}$ in the liquid phase. Preferably, controlling the input stream comprises maintaining hydrogen, oxygen and carbon dioxide in the liquid phase at a gas transfer coefficient of from 10 to 5000 h$^{-1}$, 20 to 5000 h$^{-1}$, 50 to 5000 h$^{-1}$, 100 to 5000 h$^{-1}$, 200 to 5000 h$^{-1}$, 400 to 5000 h$^{-1}$, 600 to 5000 h$^{-1}$, 800 to 5000 h$^{-1}$, 1000 to 5000 h$^{-1}$, 1500 to 5000 h$^{-1}$, 2000 to 5000 h$^{-1}$, 3000 to 5000 h$^{-1}$, 1 to 3000 h$^{-1}$, 10 to 3000 h$^{-1}$, 20 to 3000 h$^{-1}$, 50 to 3000 h$^{-1}$, 100 to 3000 h$^{-1}$, 200 to 3000 h$^{-1}$, 400 to 3000 h$^{-1}$, 600 to 3000 h$^{-1}$, 800 to 3000 h$^{-1}$, 1000 to 3000 h$^{-1}$, 1500 to 3000 h$^{-1}$, 2000 to 3000 h$^{-1}$, 1 to 2000 h$^{-1}$, 10 to 2000 h$^{-1}$, 20 to 2000 h$^{-1}$, 50 to 2000 h$^{-1}$, 100 to 2000 h$^{-1}$, 200 to 2000 h$^{-1}$, 400 to 2000 h$^{-1}$, 600 to 2000 h$^{-1}$, 800 to 2000 h$^{-1}$, 1000 to 2000 h$^{-1}$, 1500 to 2000 h$^{-1}$, 1 to 1500 h$^{-1}$, 10 to 1500 h$^{-1}$, 20 to 1500 h$^{-1}$, 50 to 1500 h$^{-1}$, 100 to 1500 h$^{-1}$, 200 to 1500 h$^{-1}$, 400 to 1500 h$^{-1}$, 600 to 1500 h$^{-1}$, 800 to 1500 h$^{-1}$, 1000 to 1500 h$^{-1}$, 1 to 1000 h$^{-1}$, 10 to 1000 h$^{-1}$, 20 to 1000 h$^{-1}$, 50 to 1000 h$^{-1}$, 100 to 1000 h$^{-1}$, 200 to 1000 h$^{-1}$, 400 to 1000 h$^{-1}$, 600 to 1000 h$^{-1}$, 800 to 1000 h$^{-1}$, 1 to 800 h$^{-1}$, 10 to 800 h$^{-1}$, 20 to 800 h$^{-1}$, 50 to 800 h$^{-1}$, 100 to 800 h$^{-1}$, 200 to 800 h$^{-1}$, 400 to 800 h$^{-1}$, 600 to 800 h$^{-1}$, 1 to 600 h$^{-1}$, 10 to 600 h$^{-1}$, 20 to 600 h$^{-1}$, 50 to 600 h$^{-1}$, 100 to 600 h$^{-1}$, 200 to 600 h$^{-1}$, 400 to 600 h$^{-1}$, 1 to 400 h$^{-1}$, 10 to 400 h$^{-1}$, 20 to 400 h$^{-1}$, 50 to 400 h$^{-1}$, 100 to 400 h$^{-1}$, 200 to 400 h$^{-1}$, 1 to 200 h$^{-1}$, 10 to 200 h$^{-1}$, 20 to 200 h$^{-1}$, 50 to 200 h$^{-1}$, 100 to 200 h$^{-1}$, 1 to 100 h$^{-1}$, 10 to 100 h$^{-1}$, 20 to 100 h$^{-1}$, 50 to 100 h$^{-1}$, 1 to 50 h$^{-1}$, 10 to 50 h$^{-1}$, 20 to 50 h$^{-1}$, 1 to 20 h$^{-1}$, 10 to 20 h$^{-1}$, or 1 to 10 h$^{31\ 1}$.

Certain specific molar ratios of inputs of gaseous substrates lead to higher levels of protein content and quality of the biomass. Preferably, controlling the input stream comprises adding a molar ratio of hydrogen:oxygen:carbon dioxide in the liquid phase of from 2 to 80:0.25 to 20:0.25 to 20. More preferably, controlling the input stream comprises adding a molar ratio of hydrogen:oxygen:carbon dioxide in the liquid phase of from 3.88 to 51.94:0.85 to 2:0.75 to 2, from 2 to 51.94:0.85 to 2:0.75 to 2, from 3 to 51.94:0.85 to 2:0.75 to 2, from 5 to 51.94:0.85 to 2:0.75 to 2, from 6 to 51.94:0.85 to 2:0.75 to 2, from 8 to 51.94:0.85 to 2:0.75 to 2, from 10 to 51.94:0.85 to 2:0.75 to 2, from 2 to 60:0.85 to 2:0.75 to 2, from 3 to 60:0.85 to 2:0.75 to 2, from 5 to 60:0.85 to 2:0.75 to 2, from 6 to 60:0.85 to 2:0.75 to 2, from 8 to 60:0.85 to 2:0.75 to 2, from 10 to 60:0.85 to 2:0.75 to 2, from 2 to 80:0.85 to 2:0.75 to 2, from 3 to 80:0.85 to 2:0.75 to 2, from 5 to 80:0.85 to 2:0.75 to 2, from 6 to 80:0.85 to 2:0.75 to 2, from 8 to 80:0.85 to 2:0.75 to 2, from 10 to 80:0.85 to 2:0.75 to 2, from 2 to 40:0.85 to 2:0.75 to 2, from 3 to 40:0.85 to 2:0.75 to 2, from 5 to 40:0.85 to 2:0.75 to 2, from 6 to 40:0.85 to 2:0.75 to 2, from 8 to 40:0.85 to 2:0.75 to 2, from 10 to 40:0.85 to 2:0.75 to 2, from 2 to 30:0.85 to 2:0.75 to 2, from 3 to 30:0.85 to 2:0.75 to 2, from 5 to 30:0.85 to 2:0.75 to 2, from 6 to 30:0.85 to 2:0.75 to 2, from 8 to 30:0.85 to 2:0.75 to 2, from 10 to 30:0.85 to 2:0.75 to 2, from 2 to 20:0.85 to 2:0.75 to 2, from 3 to 20:0.85 to 2:0.75 to 2, from 5 to 20:0.85 to 2:0.75 to 2, from 6 to 20:0.85 to 2:0.75 to 2, from 8 to 20:0.85 to 2:0.75 to 2, from 10 to 20:0.85 to 2:0.75 to 2, from 2 to 10:0.85 to 2:0.75 to 2, from 3 to 10:0.85 to 2:0.75 to 2, from 5 to 10:0.85 to 2:0.75 to 2, from 6 to 10:0.85 to 2:0.75 to 2, from 8 to 10:0.85 to 2:0.75 to 2, from 2 to 6:0.85 to 2:0.75 to 2, from 3 to 6:0.85 to 2:0.75 to 2, from 5 to 6:0.85 to 2:0.75 to 2, from 3.88 to 51.94:0.5 to 2:0.75 to 2, from 3.88 to 51.94:0.25 to 2:0.75 to 2, from 3.88 to 51.94:0.25 to 3:0.75 to 2, from 3.88 to 51.94:0.5 to 3:0.75 to 2, from 3.88 to 51.94:0.85 to 3:0.75 to 2, from 3.88 to 51.94:0.25 to 4:0.75 to 2, from 3.88 to 51.94:0.5 to 4:0.75 to 2, from 3.88 to 51.94:0.85 to 4:0.75 to 2, from 3.88 to 51.94:2 to 4:0.75 to 2, from 3.88 to 51.94:0.25 to 6:0.75 to 2, from 3.88 to 51.94:0.5 to 6:0.75 to 2, from 3.88 to 51.94:0.85 to 6:0.75 to 2, from 3.88 to 51.94:2 to 6:0.75 to 2, from 3.88 to 51.94:0.25 to 8:0.75 to 2, from 3.88 to 51.94:0.5 to 8:0.75 to 2, from 3.88 to 51.94:0.85 to 8:0.75 to 2, from 3.88 to 51.94:2 to 8:0.75 to 2, from 3.88 to 51.94:4 to 8:0.75 to 2, from 3.88 to 51.94:0.25 to 12:0.75 to 2, from 3.88 to 51.94:0.5 to 12:0.75 to 2, from 3.88 to 51.94:0.85 to 12:0.75 to 2, from 3.88 to 51.94:2 to 12:0.75 to 2, from 3.88 to 51.94:4 to 12:0.75 to 2, from 3.88 to 51.94:0.25 to 20:0.75 to 2, from 3.88 to 51.94:0.5 to 20:0.75 to 2, from 3.88 to 51.94:0.85 to 20:0.75 to 2, from 3.88 to 51.94:2 to 20:0.75 to 2, from 3.88 to 51.94:4 to 20:0.75 to 2, from 3.88 to 51.94:10 to 20:0.75 to 2, from 3.88 to 51.94:0.85 to 2:0.25 to 2, from 3.88 to 51.94:0.85 to 2:0.5 to 2, from 3.88 to 51.94:0.85 to 2:0.25 to 2.5, from 3.88 to 51.94:0.85 to 2:0.5 to 2.5, from 3.88 to 51.94:0.85 to 2:0.75 to 2.5, from 3.88 to 51.94:0.85 to 2:0.25 to 3, from 3.88 to 51.94:0.85 to 2:0.5 to 3, from 3.88 to 51.94:0.85 to 2:0.75 to 3, from 3.88 to 51.94:0.85 to 2:1 to 3, from 3.88 to 51.94:0.85 to 2:1.5 to 3, from 3.88 to 51.94:0.85 to 2:2 to 3, from 3.88 to 51.94:0.85 to 2:0.25 to 5, from 3.88 to 51.94:0.85 to 2:0.5 to 5, from 3.88 to 51.94:0.85 to 2:0.75 to 5, from 3.88 to 51.94:0.85 to 2:1 to 5, from 3.88 to 51.94:0.85 to 2:1.5 to 5, from 3.88 to 51.94:0.85 to 2:2 to 5, from 3.88 to 51.94:0.85 to 2:0.25 to 8, from 3.88 to 51.94:0.85 to 2:0.5 to 8, from 3.88 to 51.94:0.85 to 2:0.75 to 8, from 3.88 to 51.94:0.85 to 2:1 to 8, from 3.88 to 51.94:0.85 to 2:1.5 to 8, from 3.88 to 51.94:0.85 to 2:2 to 8, from 3.88 to 51.94:0.85 to 2:4 to 8, from 3.88 to 51.94:0.85 to 2:0.25 to 12, from 3.88 to 51.94:0.85 to 2:0.5 to 12, from 3.88 to 51.94:0.85 to 2:0.75 to 12, from 3.88 to 51.94:0.85 to 2:1 to 12, from 3.88 to 51.94:0.85 to 2:1.5 to 12, from 3.88 to 51.94:0.85 to 2:2 to 12, from 3.88 to 51.94:0.85 to 2:4 to 12, from 3.88 to 51.94:0.85 to 2:8 to 12, from 3.88 to 51.94:0.85 to 2:0.25 to 20, from 3.88 to 51.94:0.85 to 2:0.5 to 20, from 3.88 to 51.94:0.85 to 2:0.75 to 20, from 3.88 to 51.94:0.85 to 2:1 to 20, from 3.88 to 51.94:0.85 to 2:1.5 to 20, from 3.88 to 51.94:0.85 to 2:2 to 20, from 3.88 to 51.94:0.85 to 2:4 to 20, or from 3.88 to 51.94:0.85 to 2:8 to 20.

Carbon, preferably carbon dioxide, is preferably not metabolically limiting, and this can be controlled using a range of possible methods, including for example:

Monitoring dissolved carbon dioxide using a dissolved carbon dioxide probe and using resulting data as part of a feedback loop to maintain a concentration of about 1 mmol/l or higher by controlling the addition rates of the input gases; or Maintaining a hydrogen to carbon dioxide ratio of less than 6 and an oxygen to carbon dioxide ratio of less than 1.75 at point(s) of gas input.

With regard to adding a molar ratio of gaseous substrates, it was found that according to the invention controlling the input stream preferably comprises adding a molar ratio of hydrogen:oxygen in the liquid phase of from 0.5:1 to 12:1. More preferably, controlling the input stream comprises adding a molar ratio of hydrogen:oxygen in the liquid phase of from 0.5:1 to 10:1, from 0.5:1 to 8:1, from 0.5:1 to 6:1, from 0.5:1 to 4:1, from 0.5:1 to 2:1, from 1:1 to 12:1, from 1:1 to 10:1, from 1:1 to 9:1, from 1:1 to 8:1, from 1:1 to 7:1, from 1:1 to 6:1, from 1:1 to 5:1, from 1:1 to 4:1, from 1:1 to 3:1, from 1:1 to 2:1, from 2:1 to 12:1, from 2:1 to 10:1, from 2:1 to 8:1, from 2:1 to 6:1, from 2:1 to 4:1, from 2.5:1 to 12:1, from 2.5:1 to 10:1, from 2.5:1 to 8:1, from 2.5:1 to 6:1, from 2.5:1 to 5:1, from 2.5:1 to 4:1, from 3:1 to 12:1, from 3:1 to 10:1, from 3:1 to 8:1, from 3:1 to 6:1, from 3:1 to 4:1, from 4:1 to 12:1, from 4:1 to 10:1, from 4:1 to 8:1, from 4:1 to 6:1, from 5:1 to 12:1, from 5:1 to 10:1, from 5:1 to 8:1, from 6:1 to 12:1, from 6:1 to 10:1, or from 6:1 to 8:1. Even more preferably, controlling the input stream comprises adding a molar ratio of hydrogen:oxygen in the liquid phase of from 1:1 to 10:1, from 1:1 to 9:1, from 1:1 to 8:1, from 1:1 to 7:1, from 1:1 to 6:1 or from 1:1 to 5:1. Most preferably, controlling the input stream comprises adding a molar ratio of hydrogen:oxygen in the liquid phase of from 1.5 or 1.7:1 to 10:1, from 1.5 or 1.7:1 to 9:1, from 1.5 or 1.7:1 to 8:1, from 1.5 or 1.7:1 to 7:1, from 1.5 or 1.7:1 to 6 or 6.6:1 or from 1.5 or 1.7:1 to 5:1.

The term "gas hold-up" is defined as the volume fraction of gas in the liquid phase in the bioreactor comprising the input gases and any other gases formed in the liquid phase. Within partially or completely closed bioreactor systems and in bioreactor systems which employ gas phase and/or gas-liquid phase recirculation the gas hold-up composition ratio is preferably maintained by matching the gas input ratio with the usage ratio for the gases. In open ended systems the intended gas hold-up composition is preferably controlled by using this composition or a closely comparable composition as the average input gas composition. Thus, with regard to maintaining a molar ratio of gaseous substrates, it was found that according to the invention controlling the input stream preferably comprises maintaining a molar ratio of hydrogen:oxygen gas hold-up in the liquid phase of from 0.5:1 to 7:1. More preferably, controlling the input stream comprises maintaining a molar ratio of hydrogen:oxygen gas hold-up in the liquid phase of from 0.5:1 to 7:1, from 0.5:1 to 6:1, from 0.5:1 to 4:1, from 0.5:1 to 2:1, from 1:1 to 7:1, from 1:1 to 6:1, from 1:1 to 5:1, from 1:1 to 4:1, from 1:1 to 3:1, from 1:1 to 2:1, from 2:1 to 6:1, from 2:1 to 4:1, from 2:1 to 3 or 3.5:1, from 2.5:1 to 6:1, from 2.5:1 to 5:1, from 2.5:1 to 4:1, from 3:1 to 6:1, from 3:1 to 4:1, from 4:1 to 7:1, or from 4:1 to 6:1. Even more preferably, controlling the input stream comprises maintaining a molar ratio of hydrogen:oxygen gas hold-up in the liquid phase of from 1.2:1 to 5:1, from 1.2:1 to 4.5:1, from 1.2:1 to 4:1, from 1.2:1 to 3.5:1, from 1.2:1 to 3:1 or from 1.2:1 to 2.5:1. Most preferably, controlling the input stream comprises maintaining a molar ratio of hydrogen:oxygen gas hold-up in the liquid phase of from 1.5:1 to 2.5:1, from 1.5:1 to 3:1, from 1 or 1.5:1 to 3.5 or 4:1.

In order to obtain biomass with a high protein content and at a high production rate according to the invention it was found that oxygen as a gaseous substrate is preferably added to the liquid phase at an as high concentration as possible while also taking into account other parameters such as for example the hydrogen to oxygen ratio. Preferably, adding a molar ratio of hydrogen:oxygen in the liquid phase according to the invention comprises adding to the liquid phase oxygen in a concentration of from 5 to 100% (v/v). More preferably, adding a molar ratio of hydrogen:oxygen in the liquid phase according to the invention comprises adding to the liquid phase oxygen in a concentration of from 6, 7, 8, 9, 10, 11, 12, 13, 14, 15, 16, 17, 18, 19, 20, 25, 30, 35, 40, 45 or 50 to 100% (v/v), or from 5 to 50, 55, 60, 65, 70, 75, 80, 85, 90 or 95% (v/v). Even more preferably, adding a molar ratio of hydrogen:oxygen in the liquid phase according to the invention comprises adding to the liquid phase oxygen in a concentration of from 10 to 100% (v/v). Yet even more preferably, adding a molar ratio of hydrogen:oxygen in the liquid phase according to the invention comprises adding to the liquid phase oxygen in a concentration of from 20 to 100% (v/v).

Because of different solubilities in water of hydrogen, oxygen and carbon dioxide it is important to maintain a molar ratio of dissolved hydrogen, oxygen and carbon dioxide for optimal production of biomass. Preferably, controlling the input stream comprises maintaining a molar ratio of dissolved hydrogen:oxygen:carbon dioxide in the liquid phase of from 1 to 60:0.5 to 20:0.5 to 20. More preferably, controlling the input stream comprises maintaining a molar ratio of dissolved hydrogen:oxygen:carbon dioxide in the liquid phase of from 3.183 to 12.748:0.795 to 4.25:0.75 to 2.0, from 1 to 12.748:0.795 to 4.25:0.75 to 2.0, from 2 to 12.748:0.795 to 4.25:0.75 to 2.0, from 6 to 12.748:0.795 to 4.25:0.75 to 2.0, from 1 to 20:0.795 to 4.25:0.75 to 2.0, from 2 to 20:0.795 to 4.25:0.75 to 2.0, from 3 to 20:0.795 to 4.25:0.75 to 2.0, from 6 to 20:0.795 to 4.25:0.75 to 2.0, from 1 to 30:0.795 to 4.25:0.75 to 2.0, from 2 to 30:0.795 to 4.25:0.75 to 2.0, from 3 to 30:0.795 to 4.25:0.75 to 2.0, from 6 to 30:0.795 to 4.25:0.75 to 2.0, from 12 to 30: 0.795 to 4.25:0.75 to 2.0, from 1 to 40:0.795 to 4.25:0.75 to 2.0, from 2 to 40:0.795 to 4.25:0.75 to 2.0, from 3 to 40:0.795 to 4.25:0.75 to 2.0, from 6 to 40:0.795 to 4.25:0.75 to 2.0, from 12 to 40:0.795 to 4.25:0.75 to 2.0, from 20 to 40:0.795 to 4.25:0.75 to 2.0, from 1 to 60:0.795 to 4.25:0.75 to 2.0, from 2 to 60:0.795 to 4.25:0.75 to 2.0, from 3 to 60:0.795 to 4.25:0.75 to 2.0, from 6 to 60:0.795 to 4.25:0.75 to 2.0, from 12 to 60:0.795 to 4.25:0.75 to 2.0, from 20 to 60:0.795 to 4.25:0.75 to 2.0, from 30 to 60:0.795 to 4.25:0.75 to 2.0, from 1 to 8:0.795 to 4.25:0.75 to 2.0, from 2 to 8:0.795 to 4.25:0.75 to 2.0, from 4 to 8:0.795 to 4.25:0.75 to 2.0, from 6 to 8:0.795 to 4.25:0.75 to 2.0, from 1 to 6:0.795 to 4.25:0.75 to 2.0, from 2 to 6:0.795 to 4.25:0.75 to 2.0, from 4 to 6:0.795 to 4.25:0.75 to 2.0, from 1 to 4:0.795 to 4.25:0.75 to 2.0, from 2 to 4:0.795 to 4.25:0.75 to 2.0, from 1 to 2:0.795 to 4.25:0.75 to 2.0, from 3.183 to 12.748:0.5 to 4.25:0.75 to 2.0, from 3.183 to 12.748:1.5 to 4.25:0.75 to 2.0, from 3.183 to 12.748:2.5 to 4.25:0.75 to 2.0, from 3.183 to 12.748:0.5 to 8:0.75 to 2.0, from 3.183 to 12.748:0.795 to 8:0.75 to 2.0, from 3.183 to 12.748:1.5 to 8:0.75 to 2.0, from 3.183 to 12.748:2.5 to 8:0.75 to 2.0, from 3.183 to 12.748:4 to 8:0.75 to 2.0, from 3.183 to 12.748:0.5 to 12:0.75 to 2.0, from 3.183 to 12.748: 0.795 to 12:0.75 to 2.0, from 3.183 to 12.748:1.5 to 12:0.75 to 2.0, from 3.183 to 12.748:2.5 to 12:0.75 to 2.0, from 3.183 to 12.748:4 to 12:0.75 to 2.0, from 3.183 to 12.748:8 to 12:0.75 to 2.0, from 3.183 to 12.748:0.5 to 20:0.75 to 2.0, from 3.183 to 12.748:0.795 to 20:0.75 to 2.0, from 3.183 to 12.748:1.5 to 20:0.75 to 2.0, from 3.183 to 12.748:2.5 to 20:0.75 to 2.0, from 3.183 to 12.748:4 to 20:0.75 to 2.0, from 3.183 to 12.748:8 to 20:0.75 to 2.0, from 3.183 to 12.748:0.795 to 4.25:0.25 to 2.0, from 3.183 to 12.748:0.795 to 4.25:0.5 to 2.0, from 3.183 to 12.748:0.795 to 4.25:1.25 to 2.0, from 3.183 to 12.748:0.795 to 4.25:0.25 to 2.5, from 3.183 to 12.748:0.795 to 4.25:0.5 to 2.5, from 3.183 to 12.748:0.795 to 4.25:0.75 to 2.5, from 3.183 to 12.748:0.795 to 4.25:1.25 to 2.5, from 3.183 to 12.748:0.795 to 4.25:0.25 to 3, from 3.183 to 12.748:0.795 to 4.25:0.5 to 3, from 3.183 to 12.748:0.795 to 4.25:0.75 to 3, from 3.183 to 12.748:0.795 to 4.25:1.25 to 3, from 3.183 to 12.748:0.795 to 4.25:2 to 3, from 3.183 to 12.748:0.795 to 4.25:0.25 to 3, from 3.183 to 12.748:0.795 to 4.25:0.5 to 5, from 3.183 to 12.748:0.795 to 4.25:0.75 to 5, from 3.183 to 12.748:0.795 to 4.25:1.25 to 5, from 3.183 to 12.748: 0.795 to 4.25:2 to 5, from 3.183 to 12.748:0.795 to 4.25:3 to 5, from 3.183 to 12.748:0.795 to 4.25:0.5 to 8, from 3.183 to 12.748:0.795 to 4.25:0.75 to 8, from 3.183 to 12.748: 0.795 to 4.25:1.25 to 8, from 3.183 to 12.748:0.795 to 4.25:2 to 8, from 3.183 to 12.748:0.795 to 4.25:3 to 8, from 3.183 to 12.748:0.795 to 4.25:5 to 8, from 3.183 to 12.748:0.795 to 4.25:0.5 to 10, from 3.183 to 12.748:0.795 to 4.25:0.75 to 10, from 3.183 to 12.748:0.795 to 4.25:1.25 to 10, from 3.183 to 12.748:0.795 to 4.25:2 to 10, from 3.183 to 12.748: 0.795 to 4.25:3 to 10, from 3.183 to 12.748:0.795 to 4.25:5 to 10, from 3.183 to 12.748:0.795 to 4.25:0.5 to 15, from 3.183 to 12.748:0.795 to 4.25:0.75 to 15, from 3.183 to 12.748:0.795 to 4.25:1.25 to 15, from 3.183 to 12.748:0.795 to 4.25:2 to 15, from 3.183 to 12.748:0.795 to 4.25:3 to 15, from 3.183 to 12.748:0.795 to 4.25:5 to 15, from 3.183 to 12.748:0.795 to 4.25:10 to 15, from 3.183 to 12.748:0.795 to 4.25:0.5 to 20, from 3.183 to 12.748:0.795 to 4.25:0.75 to 20, from 3.183 to 12.748:0.795 to 4.25:1.25 to 20, from 3.183 to 12.748:0.795 to 4.25:2 to 20, from 3.183 to 12.748:0.795 to 4.25:3 to 20, from 3.183 to 12.748:0.795 to 4.25:5 to 20, or from 3.183 to 12.748:0.795 to 4.25:10 to 20.

Accordingly, controlling the input stream comprises maintaining a concentration of hydrogen of from 0.5 to 20 mg/l, a concentration of oxygen of from 0.5 to 80 mg/l and a concentration of carbon dioxide of from 20 to 2000 mg/l in the liquid phase at a temperature of from 28 to 45° C. and at a pressure in the gaseous phase of from 100 to 2000 kPa. Preferably, controlling the input stream comprises maintaining a concentration of hydrogen, oxygen and carbon dioxide of respectively from 0.5 to 20 mg/l, 0.5 to 80 mg/l and 20 to 2000 mg/l, from 2 to 20 mg/l, 0.5 to 80 mg/l and 20 to 2000 mg/l, from 5 to 20 mg/l, 0.5 to 80 mg/l and 20 to 2000 mg/l, from 10 to 20 mg/l, 0.5 to 80 mg/l and 20 to 2000 mg/l, from 0.5 to 15 mg/l, 0.5 to 10 mg/l and 50 to 250 mg/l, from 0.5 to 15 mg/l, 0.5 to 80 mg/l and 20 to 2000 mg/l, from 2 to 15 mg/l, 0.5 to 80 mg/l and 20 to 2000 mg/l, from 5 to 15 mg/l, 0.5 to 80 mg/l and 20 to 2000 mg/l, from 10 to 15 mg/l, 0.5 to 80 mg/l and 20 to 2000 mg/l, from 0.5 to 10 mg/l, 0.5 to 80 mg/l and 20 to 2000 mg/l, from 2 to 10 mg/l, 0.5 to 80 mg/l and 20 to 2000 mg/l, from 5 to 10 mg/l, 0.5 to 80 mg/l and 20 to 2000 mg/l, from 0.5 to 5 mg/l, 0.5 to 80 mg/l and 20 to 2000 mg/l, from 1.0 to 5 mg/l, 0.5 to 80 mg/l and 20 to 2000 mg/l, from 2.0 to 5 mg/l, 0.5 to 80 mg/l and 20 to 2000 mg/l, from 0.5 to 3 mg/l, 0.5 to 80 mg/l and 20 to 2000 mg/l, from 1 to 3 mg/l, 0.5 to 80 mg/l and 20 to 2000 mg/l, from 0.5 to 20 mg/l, 2 to 80 mg/l and 20 to 2000 mg/l, from 0.5 to 20 mg/l, 5 to 80 mg/l and 20 to 2000 mg/l, from 0.5 to 20 mg/l, 10 to 80 mg/l and 20 to 2000 mg/l, from 0.5 to 20 mg/l, 20 to 80 mg/l and 20 to 2000 mg/l, from 0.5 to 20 mg/l, 40 to 80 mg/l and 20 to 2000 mg/l, from 0.5 to 20 mg/l, 0.5 to 50 mg/l and 20 to 2000 mg/l, from 0.5 to 20 mg/l, 2 to 50 mg/l and 20 to 2000 mg/l, from 0.5 to 20 mg/l, 5 to 50 mg/l and 20 to 2000 mg/l, from 0.5 to 20 mg/l, 10 to 50 mg/l and 20 to 2000 mg/l, from 0.5 to 20 mg/l, 20 to 50 mg/l and 20 to 2000 mg/l, from 0.5 to 20 mg/l, 0.5 to 20 mg/l and 20 to 2000 mg/l, from 0.5 to 20 mg/l, 2 to 20 mg/l and 20 to 2000 mg/l, from 0.5 to 20 mg/l, 5 to 20 mg/l and 20 to 2000 mg/l, from 0.5 to 20 mg/l, 10 to 20 mg/l and 20 to 2000 mg/l, from 0.5 to 20 mg/l, 0.5 to 10 mg/l and 20 to 2000 mg/l, from 0.5 to 20 mg/l, 2 to 10 mg/l and 20 to 2000 mg/l, from 0.5 to 20 mg/l, 5 to 10 mg/l and 20 to 2000 mg/l, from 0.5 to 20 mg/l, 0.5 to 5 mg/l and 20 to 2000 mg/l, from 0.5 to 20 mg/l, 2 to 5 mg/l and 20 to 2000 mg/l, from 0.5 to 20 mg/l, 0.5 to 80 mg/l and 50 to 2000 mg/l, from 0.5 to 20 mg/l, 0.5 to 80 mg/l and 100 to 2000 mg/l, from 0.5 to 20 mg/l, 0.5 to 80 mg/l and 200 to 2000 mg/l, from 0.5 to 20 mg/l, 0.5 to 80 mg/l and 500 to 2000 mg/l, from 0.5 to 20 mg/l, 0.5 to 80 mg/l and 1000 to 2000 mg/l, from 0.5 to 20 mg/l, 0.5 to 80 mg/l and 20 to 1500 mg/l, from 0.5 to 20 mg/l, 0.5 to 80 mg/l and 50 to 1500 mg/l, from 0.5 to 20 mg/l, 0.5 to 80 mg/l and 100 to 1500 mg/l, from 0.5 to 20 mg/l, 0.5 to 80 mg/l and 200 to 1500 mg/l, from 0.5 to 20 mg/l, 0.5 to 80 mg/l and 500 to 1500 mg/l, from 0.5 to 20 mg/l, 0.5 to 80 mg/l and 1000 to 1500 mg/l, from 0.5 to 20 mg/l, 0.5 to 80 mg/l and 20 to 1000 mg/l, from 0.5 to 20 mg/l, 0.5 to 80 mg/l and 50 to 1000 mg/l, from 0.5 to 20 mg/l, 0.5 to 80 mg/l and 100 to 1000 mg/l, from 0.5 to 20 mg/l, 0.5 to 80 mg/l and 200 to 1000 mg/l, from 0.5 to 20 mg/l, 0.5 to 80 mg/l and 500 to 1000 mg/l, from 0.5 to 20 mg/l, 0.5 to 80 mg/l and 20 to 500 mg/l, from 0.5 to 20 mg/l, 0.5 to 80 mg/l and 50 to 500 mg/l, from 0.5 to 20 mg/l, 0.5 to 80 mg/l and 100 to 500 mg/l, from 0.5 to 20 mg/l, 0.5 to 80 mg/l and 200 to 500 mg/l, from 0.5 to 20 mg/l, 0.5 to 80 mg/l and 20 to 250 mg/l, from 0.5 to 20 mg/l, 0.5 to 80 mg/l and 50 to 250 mg/l, from 0.5 to 20 mg/l, 0.5 to 80 mg/l and 100 to 250 mg/l, from 0.5 to 20 mg/l, 0.5 to 80 mg/l and 20 to 100 mg/l, from 0.5 to 20 mg/l, 0.5 to 80 mg/l and 50 to 100 mg/l, from 0.5 to 20 mg/l, 0.5 to 80 mg/l and 20 to 50 mg/l, or from 0.5 to 20 mg/l, 0.5 to 80 mg/l and 30 to 50 mg/l.

The concentration of a dissolved gas in liquid can preferably be measured by taking a sample of the liquid under vacuum and maintaining it under vacuum up until analysis by gas chromatography. Alternative, less accurate and non-preferred methods of measuring are known in the art and comprise in-line measuring by for example optical fibre probes, impedance probes, heat transfer probes or ultrasound probes.

It was found that maintaining a minimal transfer rate of hydrogen and/or oxygen in the liquid phase is necessary for the production of a biomass comprising at least 65% protein and at a rate of at least 10 g/l/d, and preferably further for maintaining a concentration of the microorganisms in the liquid phase of the bioreactor of at least 10 g/l. Considering biomass production rate and quality alone a maximum transfer rate is in theory not required, however commercial, cost and safety considerations impose a maximum transfer rate.

Preferably, according to the invention, controlling the input stream comprises maintaining hydrogen at a transfer rate of at least 0.02 mol/l/h in the liquid phase and/or oxygen at a transfer rate of at least 0.003 mol/l/h in the liquid phase. More preferably, controlling the input stream comprises maintaining hydrogen at a transfer rate of at least 0.03, 0.04, 0.05, 0.06, 0.07, 0.08, 0.09, 0.1, 0.11, 0.12, 0.13, 0.14, 0.15, 0.16, 0.17, 0.18, 0.19, 0.2, 0.21, 0.22, 0.23, 0.24, 0.25, 0.3, 0.35, 0.4 or 0.5 mol/l/h in the liquid phase and/or oxygen at a transfer rate of at least 0.005, 0.01, 0.015, 0.02, 0.025, 0.03, 0.035, 0.04, 0.045, 0.05, 0.06, 0.07, 0.08, 0.09, 0.1, 0.11, 0.12, 0.13, 0.14, 0.15 or 0.2 mol/l/h in the liquid phase. Even more preferably, controlling the input stream comprises maintaining hydrogen at a transfer rate of at least 0.1, 0.11, 0.12, 0.13, 0.14, 0.15, 0.16, 0.17, 0.18, 0.19, 0.2, 0.21, 0.22, 0.23, 0.24, 0.25 or 0.3 mol/l/h in the liquid phase and/or oxygen at a transfer rate of at least 0.02, 0.025, 0.03, 0.035, 0.04, 0.045, 0.05, 0.06, 0.07, 0.08, 0.09, 0.1, 0.11, 0.12, 0.13, 0.14, 0.15 or 0.2 mol/l/h in the liquid phase.

Preferably, according to the invention, controlling the input stream comprises maintaining hydrogen at a transfer rate of from 0.02 to 3.0 mol/l/h in the liquid phase and/or oxygen at a transfer rate of from 0.01 to 0.4 mol/l/h in the liquid phase. More preferably, controlling the input stream comprises maintaining hydrogen at a transfer rate of from 0.04, 0.05, 0.06, 0.07, 0.08, 0.09, 0.1, 0.11, 0.12, 0.13, 0.14, 0.15, 0.16, 0.17, 0.18, 0.19, 0.2, 0.21, 0.22, 0.23, 0.24, 0.25 or 0.3 to 0.35, 0.4, 0.45, 0.5, 0.55, 0.6, 0.8, 0.9, 1.0, 1.1, 1.2, 1.3, 1.4, 1.5, 2.0 or 2.5 mol/l/h in the liquid phase and/or oxygen at a transfer rate of from 0.015, 0.02, 0.025, 0.03, 0.035, 0.04, 0.045, 0.05, 0.06, 0.07, 0.08, 0.09, 0.1, 0.11, 0.12, 0.13, 0.14, 0.15 or 0.2 to 0.25, 0.3 or 0.35 mol/l/h in the liquid phase. Even more preferably, controlling the input stream comprises maintaining hydrogen at a transfer rate of from 0.1, 0.11, 0.12, 0.13, 0.14, 0.15, 0.16, 0.17, 0.18, 0.19, 0.2, 0.21, 0.22, 0.23, 0.24, 0.25 or 0.3 to 0.35, 0.4, 0.45, 0.5, 0.55, 0.6 or 0.65 mol/l/h in the liquid phase and/or oxygen at a transfer rate of from 0.03, 0.035, 0.04, 0.045, 0.05, 0.06, 0.07 or 0.08 to 0.09, 0.1, 0.11, 0.12, 0.13, 0.14, 0.15, 0.2, 0.25 or 0.3 mol/l/h in the liquid phase. Also, more preferably, oxygen is maintained at a transfer rate of from 0.04, 0.045, 0.05, 0.06, 0.07, 0.08, 0.09, 0.1 to 0.11, 0.12, 0.13, 0.14, 0.15, 0.16, 0.18 or 0.2 mol/l/h in the liquid phase.

Preferably, the microorganisms utilise the hydrogen, oxygen, and carbon dioxide respectively at a rate of from 0.03 to 1.0 mol/g/h, 0.01 to 0.5 mol/g/h and 0.01 to 0.5 mol/g/h. More preferably, the microorganisms utilise the hydrogen, oxygen, and carbon dioxide respectively at a rate of from 0.05 to 1.0 mol/g/h, 0.01 to 0.5 mol/g/h and 0.01 to 0.5 mol/g/h, from 0.1 to 1.0 mol/g/h, 0.01 to 0.5 mol/g/h and 0.01 to 0.5 mol/g/h, from 0.2 to 1.0 mol/g/h, 0.01 to 0.5 mol/g/h and 0.01 to 0.5 mol/g/h, from 0.5 to 1.0 mol/g/h, 0.01 to 0.5 mol/g/h and 0.01 to 0.5 mol/g/h, from 0.03 to 0.5 mol/g/h, 0.01 to 0.5 mol/g/h and 0.01 to 0.5 mol/g/h, from 0.05 to 0.5 mol/g/h, 0.01 to 0.5 mol/g/h and 0.01 to 0.5 mol/g/h, from 0.1 to 0.5 mol/g/h, 0.01 to 0.5 mol/g/h and 0.01 to 0.5 mol/g/h, from 0.2 to 0.5 mol/g/h, 0.01 to 0.5 mol/g/h and 0.01 to 0.5 mol/g/h, from 0.03 to 0.2 mol/g/h, 0.01 to 0.5 mol/g/h and 0.01 to 0.5 mol/g/h, from 0.05 to 0.2 mol/g/h, 0.01 to 0.5 mol/g/h and 0.01 to 0.5 mol/g/h, from 0.03 to 1.0 mol/g/h, 0.02 to 0.5 mol/g/h and 0.01 to 0.5 mol/g/h, from 0.03 to 1.0 mol/g/h, 0.05 to 0.5 mol/g/h and 0.01 to 0.5 mol/g/h, from 0.03 to 1.0 mol/g/h, 0.1 to 0.5 mol/g/h and 0.01 to 0.5 mol/g/h, from 0.03 to 1.0 mol/g/h, 0.2 to 0.5 mol/g/h and 0.01 to 0.5 mol/g/h, from 0.03 to 1.0 mol/g/h, 0.3 to 0.5 mol/g/h and 0.01 to 0.5 mol/g/h, from 0.03 to 1.0 mol/g/h, 0.01 to 0.3 mol/g/h and 0.01 to 0.5 mol/g/h, from 0.03 to 1.0 mol/g/h, 0.02 to 0.3 mol/g/h and 0.01 to 0.5 mol/g/h, from 0.03 to 1.0 mol/g/h, 0.05 to 0.3 mol/g/h and 0.01 to 0.5 mol/g/h, from 0.03 to 1.0 mol/g/h, 0.1 to 0.3 mol/g/h and 0.01 to 0.5 mol/g/h, from 0.03 to 1.0 mol/g/h, 0.2 to 0.3 mol/g/h and 0.01 to 0.5 mol/g/h, from 0.03 to 1.0 mol/g/h, 0.01 to 0.2 mol/g/h and 0.01 to 0.5 mol/g/h, from 0.03 to 1.0 mol/g/h, 0.02 to 0.2 mol/g/h and 0.01 to 0.5 mol/g/h, from 0.03 to 1.0 mol/g/h, 0.03 to 0.2 mol/g/h and 0.01 to 0.5 mol/g/h, from 0.03 to 1.0 mol/g/h, 0.05 to 0.2 mol/g/h and 0.01 to 0.5 mol/g/h, from 0.03 to 1.0 mol/g/h, 0.1 to 0.2 mol/g/h and 0.01 to 0.5 mol/g/h, from 0.03 to 1.0 mol/g/h, 0.01 to 0.1 mol/g/h and 0.01 to 0.5 mol/g/h, from 0.03 to 1.0 mol/g/h, 0.02 to 0.1 mol/g/h and 0.01 to 0.5 mol/g/h, from 0.03 to 1.0 mol/g/h, 0.03 to 0.1 mol/g/h and 0.01 to 0.5 mol/g/h, from 0.03 to 1.0 mol/g/h, 0.05 to 0.1 mol/g/h and 0.01 to 0.5 mol/g/h, from 0.03 to 1.0 mol/g/h, 0.01 to 0.5 mol/g/h and 0.02 to 0.5 mol/g/h, from 0.03 to 1.0 mol/g/h, 0.01 to 0.5 mol/g/h and 0.05 to 0.5 mol/g/h, from 0.03 to 1.0 mol/g/h, 0.01 to 0.5 mol/g/h and 0.1 to 0.5 mol/g/h, from 0.03 to 1.0 mol/g/h, 0.01 to 0.5 mol/g/h and 0.2 to 0.5 mol/g/h, from 0.03 to 1.0 mol/g/h, 0.01 to 0.5 mol/g/h and 0.3 to 0.5 mol/g/h, from 0.03 to 1.0 mol/g/h, 0.01 to 0.5 mol/g/h and 0.01 to 0.3 mol/g/h, from 0.03 to 1.0 mol/g/h, 0.01 to 0.5 mol/g/h and 0.02 to 0.3 mol/g/h, from 0.03 to 1.0 mol/g/h, 0.01 to 0.5 mol/g/h and 0.05 to 0.3 mol/g/h, from 0.03 to 1.0 mol/g/h, 0.01 to 0.5 mol/g/h and 0.1 to 0.3 mol/g/h, from 0.03 to 1.0 mol/g/h, 0.01 to 0.5 mol/g/h and 0.2 to 0.3 mol/g/h, from 0.03 to 1.0 mol/g/h, 0.01 to 0.5 mol/g/h and 0.01 to 0.2 mol/g/h, from 0.03 to 1.0 mol/g/h, 0.01 to 0.5 mol/g/h and 0.02 to 0.2 mol/g/h, from 0.03 to 1.0 mol/g/h, 0.01 to 0.5 mol/g/h and 0.03 to 0.2 mol/g/h, from 0.03 to 1.0 mol/g/h, 0.01 to 0.5 mol/g/h and 0.05 to 0.2 mol/g/h, from 0.03 to 1.0 mol/g/h, 0.01 to 0.5 mol/g/h and 0.1 to 0.2 mol/g/h, from 0.03 to 1.0 mol/g/h, 0.01 to 0.5 mol/g/h and 0.01 to 0.1 mol/g/h, from 0.03 to 1.0 mol/g/h, 0.01 to 0.5 mol/g/h and 0.02 to 0.1 mol/g/h, from 0.03 to 1.0 mol/g/h, 0.01 to 0.5 mol/g/h and 0.03 to 0.1 mol/g/h, from 0.03 to 1.0 mol/g/h, or 0.01 to 0.5 mol/g/h and 0.05 to 0.1 mol/g/h.

More preferably, from 0.05 to 1.0 mol/g/h, 0.03 to 0.5 mol/g/h and 0.02 to 0.5 mol/g/h, from 0.1 to 1.0 mol/g/h, 0.03 to 0.5 mol/g/h and 0.02 to 0.5 mol/g/h, from 0.15 to 1.0 mol/g/h, 0.03 to 0.5 mol/g/h and 0.02 to 0.5 mol/g/h, from 0.05 to 0.5 mol/g/h, 0.03 to 0.5 mol/g/h and 0.02 to 0.5 mol/g/h, from 0.1 to 0.5 mol/g/h, 0.03 to 0.5 mol/g/h and 0.02 to 0.5 mol/g/h, from 0.15 to 0.5 mol/g/h, 0.03 to 0.5 mol/g/h and 0.02 to 0.5 mol/g/h, from 0.05 to 0.3 mol/g/h, 0.03 to 0.5 mol/g/h and 0.02 to 0.5 mol/g/h, from 0.1 to 0.3 mol/g/h, 0.03 to 0.5 mol/g/h and 0.02 to 0.5 mol/g/h, from 0.15 to 0.3 mol/g/h, 0.03 to 0.5 mol/g/h and 0.02 to 0.5 mol/g/h, from 0.05 to 1.0 mol/g/h, 0.2 to 0.5 mol/g/h and 0.02 to 0.5 mol/g/h, from 0.1 to 1.0 mol/g/h, 0.2 to 0.5 mol/g/h and 0.02 to 0.5 mol/g/h, from 0.15 to 1.0 mol/g/h, 0.2 to 0.5 mol/g/h and 0.02 to 0.5 mol/g/h, from 0.05 to 0.5 mol/g/h, 0.01 to 0.2 mol/g/h and 0.02 to 0.5 mol/g/h, from 0.1 to 0.5 mol/g/h, 0.03 to 0.2 mol/g/h and 0.02 to 0.5 mol/g/h, from 0.15 to 0.5 mol/g/h, 0.05 to 0.2 mol/g/h and 0.02 to 0.5 mol/g/h, from 0.05 to 0.3 mol/g/h, 0.01 to 0.1 mol/g/h and 0.02 to 0.5 mol/g/h, from 0.1 to 0.3 mol/g/h, 0.03 to 0.1 mol/g/h and 0.02 to 0.5 mol/g/h, from 0.15 to 0.3 mol/g/h, 0.05 to 0.1 mol/g/h and 0.02 to 0.5 mol/g/h, from 0.05 to 1.0 mol/g/h, 0.03 to 0.5 mol/g/h and 0.2 to 0.5 mol/g/h, from 0.1 to 1.0 mol/g/h, 0.03 to 0.5 mol/g/h and 0.2 to 0.5 mol/g/h, from 0.15 to 1.0 mol/g/h, 0.03 to 0.5 mol/g/h and 0.2 to 0.5 mol/g/h, from 0.05 to 0.5 mol/g/h, 0.03 to 0.5 mol/g/h and 0.01 to 0.2 mol/g/h, from 0.1 to 0.5 mol/g/h, 0.03 to 0.5 mol/g/h and 0.03 to 0.2 mol/g/h, from 0.15 to 0.5 mol/g/h, 0.03 to 0.5 mol/g/h and 0.05 to 0.2 mol/g/h, from 0.05 to 0.3 mol/g/h, 0.03 to 0.5 mol/g/h and 0.01 to 0.1 mol/g/h, from 0.1 to 0.3 mol/g/h, 0.03 to 0.5 mol/g/h and 0.03 to 0.1 mol/g/h, from 0.15 to 0.3 mol/g/h, 0.03 to 0.5 mol/g/h and 0.02 to 0.1 mol/g/h, from 0.1 to 1.0 mol/g/h, 0.05 to 0.5 mol/g/h and 0.05 to 0.5 mol/g/h, from 0.1 to 1.0 mol/g/h, 0.1 to 0.5 mol/g/h and 0.1 to 0.5 mol/g/h, from 0.4 to 1.0 mol/g/h, 0.1 to 0.3 mol/g/h and 0.1 to 0.3 mol/g/h, from 0.05 to 0.5 mol/g/h, 0.03 to 0.15 mol/g/h, 0.02 to 0.1 mol/g/h, from 0.1 to 1.0 mol/g/h, 0.08 to 0.36 mol/g/h and 0.06 to 0.26 mol/g/h, from 0.08 to 0.75 mol/g/h, 0.06 to 0.27 mol/g/h and 0.05 to 0.2 mol/g/h, from 0.08 to 0.5 mol/g/h, 0.06 to 0.18 mol/g/h and 0.05 to 0.13 mol/g/h, from 0.05 to 0.75 mol/g/h, 0.04 to 0.27 mol/g/h and 0.03 to 0.18 mol/g/h, from 0.05 to 0.6 mol/g/h, 0.04 to 0.2 mol/g/h and 0.03 to 0.15 mol/g/h, from 0.06 to 0.6 mol/g/h, 0.05 to 0.2 mol/g/h and 0.04 to 0.15 mol/g/h, from 0.06 to 0.5 mol/g/h, 0.05 to 0.18 mol/g/h and 0.04 to 0.13 mol/g/h, from 0.05 to 0.5 mol/g/h, 0.04 to 0.18 mol/g/h and 0.03 to 0.13 mol/g/h, or from 0.04 to 0.4 mol/g/h, 0.02 to 0.1 mol/g/h and 0.01 to 0.1 mol/g/h.

Gaseous substrates are typically sparged into a bioreactor from the bottom. Microorganisms present in the bioreactor utilise the gaseous substrates to produce biomass. In the present method, oxygen and hydrogen gas inputs are controlled as part of a feedback loop to allow for initial addition of the gas to the system above the explosive limit, as it is injected initially into the liquid media phase. The feedback control then ensures that oxygen and/or hydrogen is being sufficiently utilised by the system such that the gas resulting in the headspace can remain below explosive safety limits, of 5% (v/v) for oxygen and 4% (v/v) for hydrogen under standard conditions. Additionally, all three gas inputs are controlled such that oxygen or hydrogen is maintained as the limiting gas within the system.

Controlling the input stream comprises maintaining a molar ratio of dissolved hydrogen:oxygen:carbon dioxide in the liquid phase within a distance of from 0 to 750 mm from a gaseous phase, which is in direct contact with the liquid phase of from 0 to 40:0 to 15:0 to 15, from 0 to 12.748:0 to 4.25:0 to 2.0, from 3.183 to 12.748:0 to 1.0625: 0.75 to 2.0, from 0 to 3.187:0.795 to 4.25:0.75 to 2.0 or from 3.183 to 12.748:0.795 to 4.25:0 to 0.5.

Preferably, controlling the input stream comprises maintaining a molar ratio of dissolved hydrogen:oxygen:carbon dioxide in the liquid phase within a distance of from 0 to 750 mm from a gaseous phase, which is in direct contact with the liquid phase of from 1 to 12.748:0 to 1.0625:0.75 to 2.0, from 2 to 12.748:0 to 1.0625:0.75 to 2.0, from 4 to 12.748:0 to 1.0625:0.75 to 2.0, from 6 to 12.748:0 to 1.0625:0.75 to 2.0, from 8 to 12.748:0 to 1.0625:0.75 to 2.0, from 1 to 20:0 to 1.0625:0.75 to 2.0, from 2 to 20:0 to 1.0625:0.75 to 2.0, from 4 to 20:0 to 1.0625:0.75 to 2.0, from 6 to 20:0 to 1.0625:0.75 to 2.0, from 8 to 20:0 to 1.0625:0.75 to 2.0, from 12 to 20:0 to 1.0625:0.75 to 2.0, from 1 to 30:0 to 1.0625:0.75 to 2.0, from 2 to 30:0 to 1.0625:0.75 to 2.0, from 4 to 30:0 to 1.0625:0.75 to 2.0, from 6 to 30:0 to 1.0625:0.75 to 2.0, from 8 to 30:0 to 1.0625:0.75 to 2.0, from 12 to 30:0 to 1.0625:0.75 to 2.0, from 20 to 30:0 to 1.0625:0.75 to 2.0, from 1 to 40:0 to 1.0625:0.75 to 2.0, from 2 to 40:0 to 1.0625:0.75 to 2.0, from 4 to 40:0 to 1.0625:0.75 to 2.0, from 6 to 40:0 to 1.0625:0.75 to 2.0, from 8 to 40:0 to 1.0625:0.75 to 2.0, from 12 to 40:0 to 1.0625:0.75 to 2.0, from 20 to 40:0 to 1.0625:0.75 to 2.0, from 1 to 8:0 to 1.0625:0.75 to 2.0, from 2 to 8:0 to 1.0625:0.75 to 2.0, from 4 to 8:0 to 1.0625:0.75 to 2.0, from 6 to 8:0 to 1.0625:0.75 to 2.0, from 1 to 6:0 to 1.0625:0.75 to 2.0, from 2 to 6:0 to 1.0625:0.75 to 2.0, from 4 to 6:0 to 1.0625:0.75 to 2.0, from 1 to 4:0 to 1.0625:0.75 to 2.0, from 2 to 4:0 to 1.0625:0.75 to 2.0, from 3.183 to 12.748:0 to 1.0625:0.25 to 2.0, from 3.183 to 12.748:0 to 1.0625:0.5 to 2.0, from 3.183 to 12.748:0 to 1.0625:1 to 2.0, from 3.183 to 12.748:0 to 1.0625:0.25 to 2.5, from 3.183 to 12.748:0 to 1.0625:0.5 to 2.5, from 3.183 to 12.748:0 to 1.0625:1 to 2.5, from 3.183 to 12.748:0 to 1.0625:2 to 2.5, from 3.183 to 12.748:0 to 1.0625:0.25 to 3.5, from 3.183 to 12.748:0 to 1.0625:0.5 to 3.5, from 3.183 to 12.748:0 to 1.0625:1 to 3.5, from 3.183 to 12.748:0 to 1.0625:2 to 3.5, from 3.183 to 12.748:0 to 1.0625:0.25 to 5, from 3.183 to 12.748:0 to 1.0625:0.5 to 5, from 3.183 to 12.748:0 to 1.0625:1 to 5, from 3.183 to 12.748:0 to 1.0625:2 to 5, from 3.183 to 12.748:0 to 1.0625:3.5 to 5, 0.25 to 10, from 3.183 to 12.748:0 to 1.0625:0.5 to 10, from 3.183 to 12.748:0 to 1.0625:1 to 10, from 3.183 to 12.748:0 to 1.0625:2 to 10, from 3.183 to 12.748:0 to 1.0625:3.5 to 10, from 3.183 to 12.748:0 to 1.0625:5 to 10, from 3.183 to 12.748:0 to 1.0625:0.25 to 15, from 3.183 to 12.748:0 to 1.0625:0.5 to 15, from 3.183 to 12.748:0 to 1.0625:1 to 15, from 3.183 to 12.748:0 to 1.0625:2 to 15, from 3.183 to 12.748:0 to 1.0625:3.5 to 15, from 3.183 to 12.748:0 to 1.0625:5 to 15, from 3.183 to 12.748:0 to 1.0625:10 to 15, from 3.183 to 12.748:0 to 1.0625:0.25 to 1.0, from 3.183 to 12.748:0 to 1.0625:0.5 to 1.0, or from 3.183 to 12.748:0 to 1.0625:0.75 to 1.0.

Preferably, controlling the input stream comprises maintaining a molar ratio of dissolved hydrogen:oxygen:carbon dioxide in the liquid phase within a distance of from 0 to 750 mm from a gaseous phase, which is in direct contact with the liquid phase of from 0 to 3.187:0.25 to 4.25:0.75 to 2.0, from 0 to 3.187:1.5 to 4.25:0.75 to 2.0, from 0 to 3.187:2.5 to 4.25:0.75 to 2.0, from 0 to 3.187:0.25 to 6:0.75 to 2.0, from 0 to 3.187:0.795 to 6:0.75 to 2.0, from 0 to 3.187:1.5 to 6:0.75 to 2.0, from 0 to 3.187:2.5 to 6:0.75 to 2.0, from 0 to 3.187:0.25 to 10:0.75 to 2.0, from 0 to 3.187:0.795 to 10:0.75 to 2.0, from 0 to 3.187:1.5 to 10:0.75 to 2.0, from 0 to 3.187:2.5 to 10:0.75 to 2.0, from 0 to 3.187:5 to 10:0.75 to 2.0, from 0 to 3.187:0.25 to 15:0.75 to 2.0, from 0 to 3.187:0.795 to 15:0.75 to 2.0, from 0 to 3.187:1.5 to 15:0.75 to 2.0, from 0 to 3.187:2.5 to 15:0.75 to 2.0, from 0 to 3.187:5 to 15:0.75 to 2.0, from 0 to 3.187:10 to 15:0.75 to 2.0, from 0 to 3.187:0.25 to 3:0.75 to 2.0, from 0 to 3.187:0.795 to 3:0.75 to 2.0, from 0 to 3.187:1.5 to 3:0.75 to 2.0, from 0 to 3.187:2.5 to 3:0.75 to 2.0, from 0 to 3.187:0.25 to 2:0.75 to 2.0, from 0 to 3.187:0.795 to 2:0.75 to 2.0, from 0 to 3.187:1.5 to 2:0.75 to 2.0, from 0 to 3.187:0.25 to 1.5:0.75 to 2.0, from 0 to 3.187:0.795 to 1.5:0.75 to 2.0, from 0 to 3.187:0.25 to 1:0.75 to 2.0, from 0 to 3.187:0.795 to 1:0.75 to 2.0, from 0 to 3.187:0.795 to 4.25:0.25 to 2.0, from 0 to 3.187:0.795 to 4.25:0.5 to 2.0, from 0 to 3.187:0.795 to 4.25:1 to 2.0, from 0 to 3.187:0.795 to 4.25:0.25 to 2.5, from 0 to 3.187:0.795 to 4.25:0.5 to 2.5, from 0 to 3.187:0.795 to 4.25:1 to 2.5, from 0 to 3.187:0.795 to 4.25:2 to 2.5, from 0 to 3.187:0.795 to 4.25:0.25 to 3.5, from 0 to 3.187:0.795 to 4.25:0.5 to 3.5, from 0 to 3.187:0.795 to 4.25:1 to 3.5, from 0 to 3.187:0.795 to 4.25:2 to 3.5, from 0 to 3.187:0.795 to 4.25:0.25 to 5, from 0 to 3.187:0.795 to 4.25:0.5 to 5, from 0 to 3.187:0 to 1.0625:1 to 5, from 0 to 3.187:0.795 to 4.25:2 to 5, from 0 to 3.187:0.795 to 4.25:3.5 to 5, 0.25 to 10, from 0 to 3.187:0.795 to 4.25:0.5 to 10, from 0 to 3.187:0.795 to 4.25:1 to 10, from 0 to 3.187:0.795 to 4.25:2 to 10, from 0 to 3.187:0.795 to 4.25:3.5 to 10, from 0 to 3.187:0.795 to 4.25:5 to 10, 0.25 to 15, from 0 to 3.187:0.795 to 4.25:0.5 to 15, from 0 to 3.187:0.795 to 4.25:1 to 15, from 0 to 3.187:0.795 to 4.25:2 to 15, 0 to 3.187:0.795 to 4.25:3.5 to 15, from 0 to 3.187:0.795 to 4.25:5 to 15, from 0 to 3.187:0.795 to 4.25:10 to 15, from 0 to 3.187:0.795 to 4.25:0.25 to 1.0, from 0 to 3.187:0.795 to 4.25:0.5 to 1.0, or from 0 to 3.187:0.795 to 4.25:0.75 to 1.0.

Preferably, controlling the input stream comprises maintaining a molar ratio of dissolved hydrogen:oxygen:carbon dioxide in the liquid phase within a distance of from 0 to 750 mm from a gaseous phase, which is in direct contact with the liquid phase of from 3.183 to 12.748:0.795 to 4.25:0 to 0.5 from 1 to 12.748:0.795 to 4.25:0 to 0.5, from 2 to 12.748:0.795 to 4.25:0 to 0.5, from 4 to 12.748:0.795 to 4.25:0 to 0.5, from 6 to 12.748:0.795 to 4.25:0 to 0.5, from 8 to 12.748:0.795 to 4.25:0 to 0.5, from 1 to 20:0.795 to 4.25:0 to 0.5, from 2 to 20:0.795 to 4.25:0 to 0.5, from 4 to 20:0.795 to 4.25:0 to 0.5, from 6 to 20:0.795 to 4.25:0 to 0.5, from 8 to 20:0.795 to 4.25:0 to 0.5, from 12 to 20:0.795 to 4.25:0 to 0.5, from 1 to 30:0.795 to 4.25:0 to 0.5, from 2 to 30:0.795 to 4.25:0 to 0.5, from 4 to 30:0.795 to 4.25:0 to 0.5, from 6 to 30:0.795 to 4.25:0 to 0.5, from 8 to 30:0.795 to 4.25:0 to 0.5, from 12 to 30:0.795 to 4.25:0 to 0.5, from 20 to 30:0.795 to 4.25:0 to 0.5, from 1 to 40:0.795 to 4.25:0 to 0.5, from 2 to 40:0.795 to 4.25:0 to 0.5, from 4 to 40:0.795 to 4.25:0 to 0.5, from 6 to 40:0.795 to 4.25:0 to 0.5, from 8 to 40:0.795 to 4.25:0 to 0.5, from 12 to 40:0.795 to 4.25:0 to 0.5, from 20 to 40:0.795 to 4.25:0 to 0.5, from 1 to 8:0.795 to 4.25:0 to 0.5, from 2 to 8:0.795 to 4.25:0 to 0.5, from 4 to 8:0.795 to 4.25:0 to 0.5, from 6 to 8:0.795 to 4.25:0 to 0.5, from 1 to 6:0.795 to 4.25:0 to 0.5, from 2 to 6:0.795 to 4.25:0 to 0.5, from 4 to 6:0.795 to 4.25:0 to 0.5, from 1 to 4:0.795 to 4.25:0 to 0.5, from 2 to 4:0.795 to 4.25:0 to 0.5, from 3.183 to 12.748:0.25 to 4.25:0 to 0.5, from 3.183 to 12.748: 1.5 to 4.25:0 to 0.5, from 3.183 to 12.748:2.5 to 4.25:0 to 0.5, from 3.183 to 12.748:0.25 to 6:0 to 0.5, from 3.183 to 12.748:0.795 to 6:0 to 0.5, from 3.183 to 12.748:1.5 to 6:0 to 0.5, from 3.183 to 12.748:2.5 to 6:0 to 0.5, from 3.183 to 12.748:0.25 to 10:0 to 0.5, from 3.183 to 12.748:0.795 to 10:0 to 0.5, from 3.183 to 12.748:1.5 to 10:0 to 0.5, from 3.183 to 12.748:2.5 to 10:0 to 0.5, from 3.183 to 12.748:5 to 10:0 to 0.5, from 3.183 to 12.748:0.25 to 15:0 to 0.5, from 3.183 to 12.748:0.795 to 15:0 to 0.5, from 3.183 to 12.748:1.5 to 15:0 to 0.5, from 3.183 to 12.748:2.5 to 15:0 to 0.5, from 3.183 to 12.748:5 to 15:0 to 0.5, from 3.183 to 12.748:10 to 15:0 to 0.5, from 3.183 to 12.748:0.25 to 3:0 to 0.5, from 3.183 to 12.748:0.795 to 3:0 to 0.5, from 3.183 to 12.748:1.5 to 3:0 to 0.5, from 3.183 to 12.748:2.5 to 3:0 to 0.5, from 3.183 to 12.748:0.25 to 2:0 to 0.5, from 3.183 to 12.748:0.795 to 2:0 to 0.5, from 3.183 to 12.748:1.5 to 2:0 to 0.5, from 3.183 to 12.748:0.25 to 1.5:0 to 0.5, from 3.183 to 12.748:0.795 to 1.5:0 to 0.5, from 3.183 to 12.748:0.25 to 1:0 to 0.5, or from 3.183 to 12.748:0.795 to 1:0 to 0.5.

As mentioned above, controlling the input stream comprises maintaining a molar ratio of dissolved hydrogen:oxygen:carbon dioxide in the liquid phase within a distance of from 0 to 750 mm from a gaseous phase, which is in direct contact with the liquid phase. More preferably, the distance comprises of from 0 to 700 mm, from 0 to 650 mm, from 0 to 600 mm, from 0 to 550 mm, from 0 to 500 mm, from 0 to 450 mm, from 0 to 400 mm, from 0 to 350 mm, from 0 to 300 mm, from 0 to 250 mm, from 0 to 200 mm, from 0 to 150 mm, from 0 to 100 mm, from 0 to 90 mm, from 0 to 80 mm, from 0 to 70 mm, from 0 to 60 mm, from 0 to 50 mm, from 0 to 40 mm, from 0 to 30 mm, from 0 to 20 mm, or from 0 to 10 mm.

The method according to the invention is preferably executed by using a bioreactor suitable for use in an industrial setting. Preferably, the bioreactor according to the invention is a chemostat.

A bioreactor suitable for use in an industrial setting adheres to standard requirements in the field of industrial fermentation of microorganisms, preferably hydrogen-oxidising microorganisms. A bioreactor suitable for use in an industrial setting typically has a liquid phase volume of about 0.2 to about 10 $m^3$ for a pilot scale bioreactor and about 2 to about 500 $m^3$ for a plant scale bioreactor, but in theory has no upper limit volume. Standard requirements in the field of industrial fermentation of microorganisms preferably comprise the ability to withstand high thermal stresses and/or high internal gaseous and liquid pressures. Standard requirements according to the invention comprise design considerations to prevent and/or withstand the consequences of potentially explosive gas mixtures comprising hydrogen and oxygen. A bioreactor suitable for use in an industrial setting according to the invention therefore enables the use of high concentrations of gaseous substrates such as hydrogen and/or oxygen according to the invention.

In the context of the invention the bioreactor, and preferably the chemostat, can be used to maintain the physiological status and the specific growth rate of the microorganisms substantially static. This is achieved by maintaining various continuous (bio)chemical processes by for example controlling agitation speed, gaseous substrate transfer rate, dilution rate (volumetric flow of supplied nutrients divided by the total volume), temperature, pH, removing culture medium comprising microorganisms and/or adding culture medium, preferably to maintain a substantially constant liquid medium culture volume. For example, by changing the rate with which medium is added to the bioreactor the specific growth rate of the microorganisms can be controlled. Increasing the dilution rate will increase the growth of the microorganisms. However, the dilution rate needs to be controlled relative to the specific growth rate to prevent wash-out. The dilution rate is controlled in order to maximize the protein production rate and protein content of the microorganisms. When the specific growth rate of the microorganisms is too high the protein content and/or quality of the biomass can be reduced.

Bioreactors for executing the method according to the invention are preferably selected from the group comprising bubble column, air lift, continuous stirred-tank and loop-type reactors. A preferred bioreactor for executing the method according to the invention is a continuous stirred-tank reactor. Preferably, the bioreactor comprises one or more gas and/or liquid recycle systems.

The rationale behind replacement of the liquid phase within the bioreactor leading to higher levels of protein content and quality of the biomass is to maintain the microorganisms in a physiological steady state under constant environmental conditions. In this steady state, growth occurs at a substantially constant specific growth rate and all culture parameters such as pH, nutrient concentrations, gaseous substrate concentrations, microorganism concentrations, remain substantially constant. It was found that such a physiological steady state of the microorganisms is necessary for the production of a biomass comprising at least 65% protein and at a rate of more than 10 g/l/d. Thus, according to the invention, the input stream and nutrient composition are preferably controlled to maintain a specific growth rate and/or steady state of the microorganisms, preferably a steady state of the microorganisms, more preferably a specific growth rate of the microorganisms.

According to the invention, the input stream and nutrient composition are preferably controlled to achieve or maintain the steady state of the microorganisms by maintaining a concentration of the microorganisms in the liquid phase of the bioreactor of at least 5 g/l, preferably of from 5 to 100 g/l. More preferably, the steady state of the microorganisms can be achieved or maintained by maintaining a concentration of the microorganisms in the liquid phase of the bioreactor of at least 6, 7, 8, 9, 10 to 11, 12, 13, 14, 15, 16, 17, 18, 19, 20, 25 or 30 g/l, preferably of from 6, 7, 8, 9, 10 to 11, 12, 13, 14, 15, 16, 17, 18, 19, 20, 25 or 30 to 50, 60, 70, 80, 90 or 100 g/l. Even more preferably, the steady state of the microorganisms can be achieved or maintained by maintaining a concentration of the microorganisms in the liquid phase of the bioreactor of from at least 8, 9, 10 to 11, 12, 13, 14 or 15 g/l, preferably of from 8, 9, 10 to 11, 12, 13, 14 or 15 to 25, 30, 35, 40, 45 or 50 g/l.

Preferably, controlling the input stream and nutrient composition according to the invention comprises maintaining a specific growth rate of the microorganisms of at least 1.0 $d^{-1}$, preferably at least 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9 or 4.0 $d^{-1}$. More preferably, controlling the input stream and nutrient composition according to the invention comprises maintaining a specific growth rate of the microorganisms of at least 1.5, 1.6, 1.7, 1.8, 1.9, 2.0, 2.1, 2.2, 2.3, 2.4 or 2.5 $d^{-1}$. Preferably, controlling the input stream and nutrient composition according to the invention comprises maintaining a specific growth rate of the microorganisms of at least 0.03 $h^{-1}$, preferably at least 0.03, 0.04, 0.05, 0.06, 0.07, 0.08, 0.09, 0.1, 0.11, 0.12, 0.13, 0.14, 0.15, 0.16, 0.17, 0.18, 0.2, 0.21, 0.22, 0.23, 0.24, 0.25 or 0.3 $h^{-1}$. More preferably, controlling the input stream and nutrient composition according to the invention comprises maintaining a specific growth rate of the microorganisms of at least 0.05, 0.06, 0.07, 0.08, 0.09 or 0.1 $h^{-1}$.

When the specific growth rate of the microorganisms is too high the protein content and/or quality of the biomass can be reduced. For example, the nucleic acid content of the biomass can become too high.

Thus preferably, controlling the input stream and nutrient composition according to the invention comprises maintaining a specific growth rate of the microorganisms of from 1.0 to 8.0 $d^{-1}$. More preferably controlling the input stream and nutrient composition comprises maintaining a specific growth rate of the microorganisms of from 1.1, 1.2, 1.3, 1.4, 1.5, 1.6, 1.7, 1.8, 1.9 or 2.0 to 3.0, 3.1, 3.2, 3.3, 3.4, 3.5, 3.6, 3.7, 3.8, 3.9, 4.0, 4.5, 5.0, 5.5, 6.0 or 7.0 $d^{-1}$. Even more preferably controlling the input stream and nutrient composition comprises maintaining a specific growth rate of the microorganisms of from 1.5, 1.6, 1.7, 1.8, 1.9, 2.0, 2.1, 2.2, 2.3, 2.4 to 2.6, 2.7, 2.8, 2.9, 3.0, 3.1, 3.2, 3.3, 3.4 or 3.5 $d^{-1}$. Preferably, controlling the input stream and nutrient composition according to the invention comprises maintaining a specific growth rate of the microorganisms of from 0.03 to 0.4 $h^{-1}$. More preferably controlling the input stream and nutrient composition comprises maintaining a specific growth rate of the microorganisms of from 0.04, 0.05, 0.06, 0.07, 0.08, 0.09 or 0.1 to 0.11, 0.12, 0.13, 0.14, 0.15, 0.16, 0.17, 0.18, 0.19, 0.2, 0.25, 0.3 or 0.35 $h^{-1}$. Even more preferably controlling the input stream and nutrient composition comprises maintaining a specific growth rate of the microorganisms of from 0.05, 0.06, 0.07, 0.08 or 0.09 to 0.11, 0.12, 0.13, 0.14, 0.15, 0.16, 0.17, 0.18, 0.19 or 0.2 $h^{-1}$.

The applicants have surprisingly found that bacteria selected from the genus *Alcaligines* sp are capable of producing high quality biomass at a high rate of productivity. Accordingly, the present invention relates to a method of producing biomass from bacteria selected from the genus *Alcaligines* sp. The applicants have surprisingly found that bacteria selected from the genus *Cupriavidus* sp are capable of producing an even higher quality biomass at an even higher rate of productivity. Accordingly, the present invention relates to a method of producing biomass from bacteria selected from the genus *Cupriavidus* sp, preferably the species *Cupriavidus necator*. Preferably, the biomass comprises at least 65% protein of total biomass by dry weight. Preferably, the biomass is produced at a rate of more than 10 g/l/d. Preferably, the method of producing biomass comprises using one or more input streams comprising one or more gaseous substrates, comprising hydrogen, oxygen and/or carbon dioxide, comprising contacting the microorganisms in a liquid phase with a nutrient composition comprising carbon, nitrogen and/or phosphorous comprising compounds and the gaseous substrates wherein the input stream and nutrient composition are controlled. The present invention also relates to a method of producing biomass from bacteria selected from the genus *Alcaligines* sp., isolating the produced biomass and removing the nutrient composition, comprising downstream processing. The present invention also relates to a method of producing biomass from bacteria selected from the genus *Cupriavidus* sp, preferably the species *Cupriavidus necator*, isolating the produced biomass and removing the nutrient composition, comprising downstream processing.

For further application of the produced biomass as, for example, a source of nutrients for other organisms it is necessary to process the produced biomass. Removing the nutrient composition and the water component of the produced biomass is commonly done in the agricultural food industry. For ease of transport, storage and prevention of contamination by pathogens or other undesirable organisms the water content of the produced biomass for further application needs to be as low as possible. Accordingly, the present invention also relates to a method of isolating the biomass produced according to the method of the invention and removing the nutrient composition, comprising downstream processing. In addition, the present invention relates to a method of isolating the biomass produced according to the invention and removing the nutrient composition, comprising dewatering and/or drying the biomass such that the biomass comprises a water content of less than 10% by weight. Preferably, the biomass comprises a water content of less than 9.0%, 8.0%, 7.0%, 6.5%, 6.0%, 5.5%, 5.0%, 4.5%, 4.0%, 3.5%, 3.0%, 2.5%, 2.0%, 1.5%, 1.0% or 0.5% by weight.

The nutrient composition obtained by isolating the biomass produced according to the method of the invention and removing the nutrient composition, comprising downstream processing or by isolating the biomass produced according to the invention and removing the nutrient composition, comprising dewatering and/or drying the biomass such that the biomass comprises a water content of less than 10%, 9.0%, 8.0%, 7.0%, 6.5%, 6.0%, 5.5%, 5.0%, 4.5%, 4.0%, 3.5%, 3.0%, 2.5%, 2.0%, 1.5%, 1.0% or 0.5% by weight can be used as a nutrient composition for producing biomass according to the method of the present invention.

The biomass produced or obtained by any of the methods in the present disclosure, can be used to feed or provide nutrition to one or more organisms. The agricultural industry typically uses similar feed in organisms such as fish, crustaceans, molluscs, poultry, pigs and cattle. Therefore, the present invention also relates to use of the biomass produced or obtained by any of the methods in the present disclosure to feed or provide nutrition to, for example, fish, crustaceans, molluscs, poultry, pigs and cattle. Preferably, the fish comprise *Cyprinidae, Salmonidae, Thunnini, Oreochromis* and *Siluriformes*. Preferably, the poultry comprise *Gallus gallus domesticus*.

The properties of biomass produced by chemoautotrophic bacteria directly relate to its value for certain applications. For example, for animal feed and food applications, protein content and amino acid composition are essential for nutritional quality. The method of the present invention produces such a biomass of high nutritional quality. Therefore, the invention further relates to biomass obtainable by the method of the present invention comprising protein comprising an amino acid content comprising a histidine content of from 0.6 to 6.4% of total biomass dry weight protein content, an isoleucine content of from 1.3 to 9.2% of total biomass dry weight protein content, a leucine content of from 2.5 to 16.0% of total biomass dry weight protein content, a lysine content of from 2.0 to 14.8% of total biomass dry weight protein content, a methionine content of from 0.7 to 7.2% of total biomass dry weight protein content, a phenylalanine content of from 1.2 to 11.4% of total biomass dry weight protein content, a threonine content of from 1.1 to 9.2% of total biomass dry weight protein content, a tryptophan content of from 0.3 to 5.2% of total biomass dry weight protein content, and a valine content of from 1.1 to 12.4% of total biomass dry weight protein content. Preferably, the amino acid content comprises a histidine content of from 0.9 to 4.8% of total biomass dry weight protein content, an isoleucine content of from 2.0 to 6.9% of total biomass dry weight protein content, a leucine content of from 3.8 to 12.0% of total biomass dry weight protein content, a lysine content of from 3.0 to 11.1% of total biomass dry weight protein content, a methionine content of from 1.1 to 5.4% of total biomass dry weight protein content, a phenylalanine content of from 1.7 to 8.5% of total biomass dry weight protein content, a threonine content of from 1.6 to 6.9% of total biomass dry weight protein content, a tryptophan content of from 0.4 to 3.9% of total biomass dry weight protein content, and a valine content of from 1.7 to 9.3% of total biomass dry weight protein content. More preferably, the amino acid content comprises a histidine content of from 1.2 to 3.2% of total biomass dry weight protein content, an isoleucine content of from 2.6 to 4.6% of total biomass dry weight protein content, a leucine content of from 5.0 to 8.0% of total biomass dry weight protein content, a lysine content of from 4.0 to 7.4% of total biomass dry weight protein content, a methionine content of from 1.4 to 3.6% of total biomass dry weight protein content, a phenylalanine content of from 2.3 to 5.7% of total biomass dry weight protein content, a threonine content of from 2.1 to 4.6% of total biomass dry weight protein content, a tryptophan content of from 0.5 to 2.6% of total biomass dry weight protein content, and a valine content of from 2.2 to 6.2% of total biomass dry weight protein content.

In addition, the invention relates to biomass obtainable by the method of the present invention, comprising a lipid content of from 1.5 to 24% of total biomass dry weight comprising a fatty acid content comprising a C16:0 palmitic acid content of from 15 to 80% of total biomass dry weight fatty acid content, a C16:1 palmitoleic acid content of from 2.5 to 30% of total biomass dry weight fatty acid content, and a C17:1 heptadecenoic acid content of from 15 to 80% of total biomass dry weight fatty acid content. Preferably, the lipid content comprises of from 2.3 to 18% of total biomass dry weight comprising a fatty acid content comprising a C16:0 palmitic acid content of from 23 to 60% of total biomass dry weight fatty acid content, a C16:1 palmitoleic acid content of from 3.8 to 22.3% of total biomass dry weight fatty acid content, and a C17:1 heptadecenoic acid content of from 23 to 60% of total biomass dry weight fatty acid content. More preferably, the lipid content comprises of from 3 to 12% of total biomass dry weight comprising a fatty acid content comprising a C16:0 palmitic acid content of from 30 to 40% of total biomass dry weight fatty acid content, a C16:1 palmitoleic acid content of from 5 to 15% of total biomass dry weight fatty acid content, and a C17:1 heptadecenoic acid content of from 30 to 40% of total biomass dry weight fatty acid content.

DETAILED DESCRIPTION OF THE FIGURES

The invention will now be discussed with reference to the figures, which show preferred exemplary embodiments of the subject invention.

Figure 1:
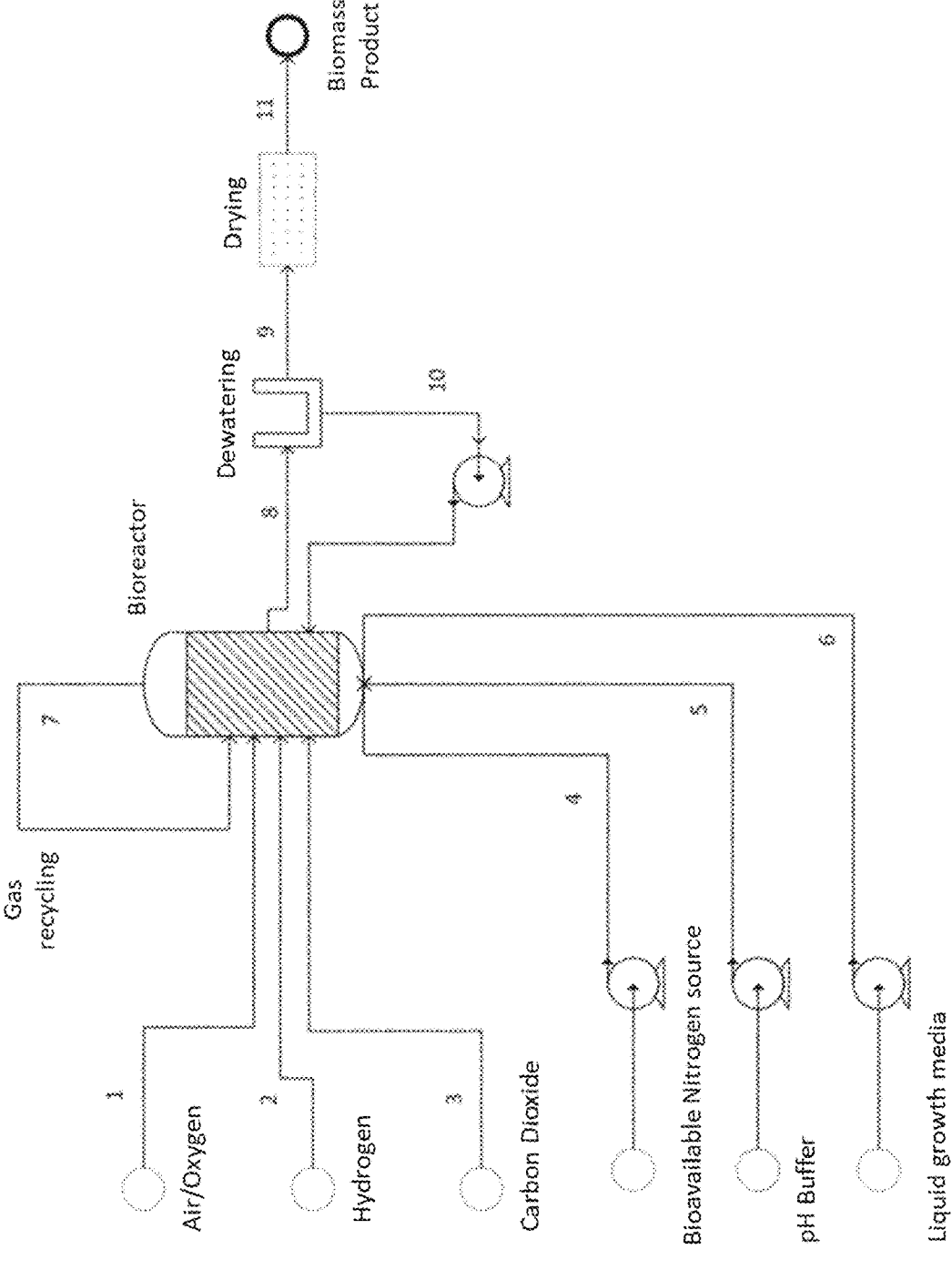

FIG. 1 shows a preferred embodiment of the present invention. Herein, in a reactor flow chart, wherein the numerals represent the following features: A feedback loop control of oxygen/air input (1), hydrogen input (2), and carbon dioxide input (3) based on through-gas analysis and/or analysis of their concentrations in the bioreactor is controlled through a defined and adjustable input gas ratio for optimal protein production metabolism. pH and OD based feedback loops for inorganic nitrogen (e.g. urea) addition (4) per unit biomass produced and maintenance of pH through addition of a pH buffer (5) are also present. Liquid growth media (6) is added to the bioreactor as needed in response to growth of the microorganisms measured through the sensors of the various feedback loops. Unutilised gas may be recycled (7) into the bioreactor. A further feature, the dilution rate, allows to reach a certain maintenance time in the reactor, an optimal growth of the microorganisms, and an optimal production of biomass. The dilution rate is determined by controlling the inputs of inorganic nitrogen (4), pH buffer (5), liquid growth media (6), and the recycling of removed liquid containing biomass (10) and the output of the removal of liquid containing biomass (8). Removal of liquid containing biomass (8) is followed by a downstream processing step involving dewatering in which a large part of the liquid is separated from the liquid containing biomass. The large part of the liquid is then preferably recycled (10) to the bioreactor, while the biomass together with a small part of the remaining liquid is subjected to additional downstream processing steps (9) comprising further dewatering, drying and inactivation of the microorganisms, which via optional additional downstream processing steps (11) ultimately results in a biomass product preferably suitable as a source of nutrition for other organisms. Improved overall system productivity may be achieved by enabling higher oxygen concentrations, and thereby reduced oxygen limitation, within the overall system. Responsive oxygen feeding (1) is preferred to improve reactor load while remaining within safe gas mixture concentrations within the headspace. Oxygen preferably remains at less than 5% in the headspace of the system but is added at increasing volumes in response to increased consumption of the gas by the microbes, to achieve optimal balancing of protein production and growth rate. The maximum protein yield requires optimal availability of inorganic nitrogen compounds, such as ammonia, and/or urea, to the system. By feeding in ammonia (4) in response to defined process conditions, an optimal growth rate can also be achieved.

Together the fine control of all parameters allows for improved overall productivity of the fermentation by reducing and optimizing substrate limitations. Without these limitations the fermentation is able to achieve higher productivities, and crucially the control aspects have been developed to balance this improved productivity against optimization of the protein content of the biomass.

Figure 2:
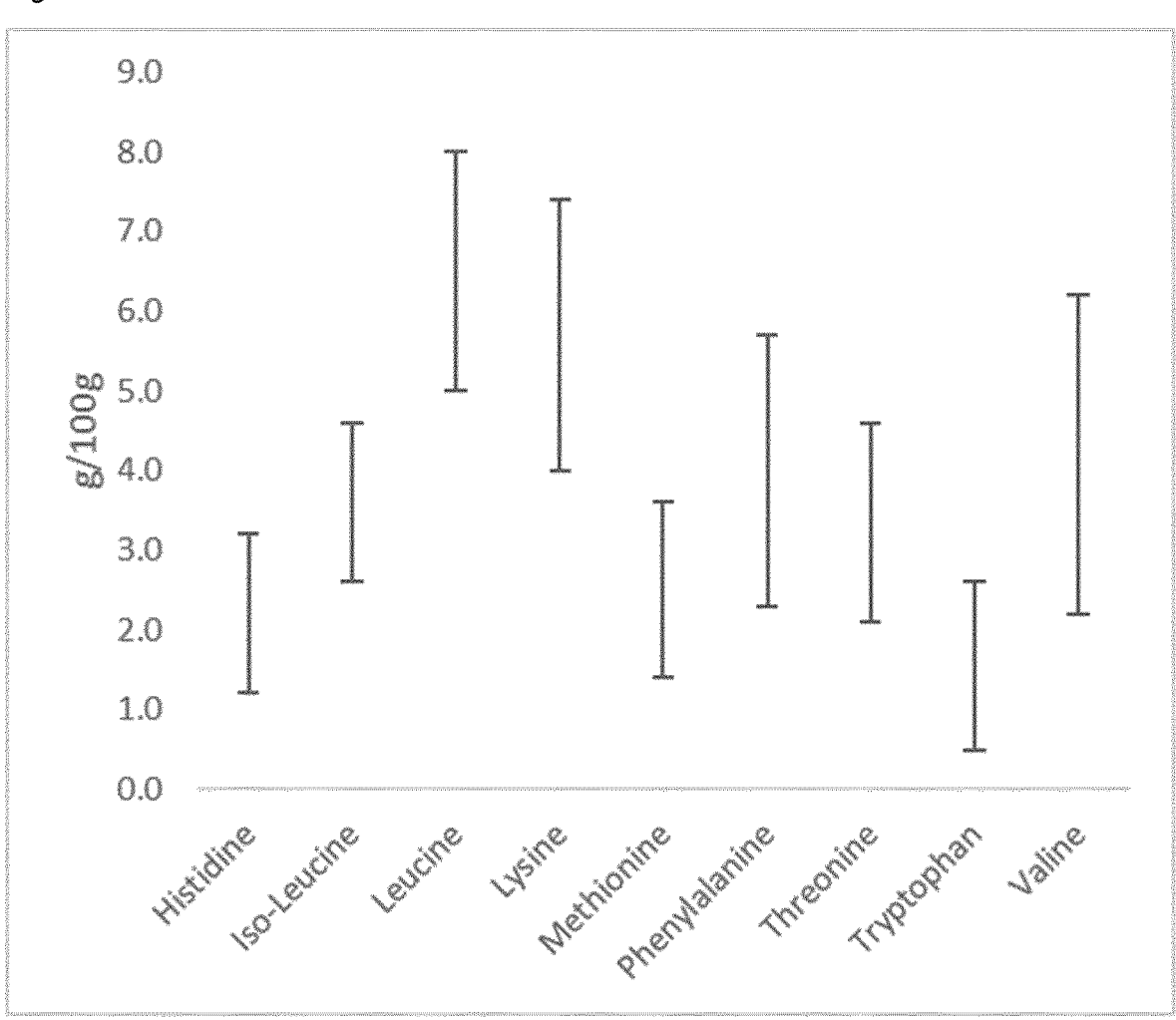
FIG. 2 shows an example of the ranges of amounts of the essential amino acids per 100 g of the total protein content of isolated biomass produced according to the method of the invention.

FIG. 2 shows an example of the ranges of amounts of the essential amino acids per 100 g of the total protein content of isolated biomass produced according to the method of the invention.

Figure 3:
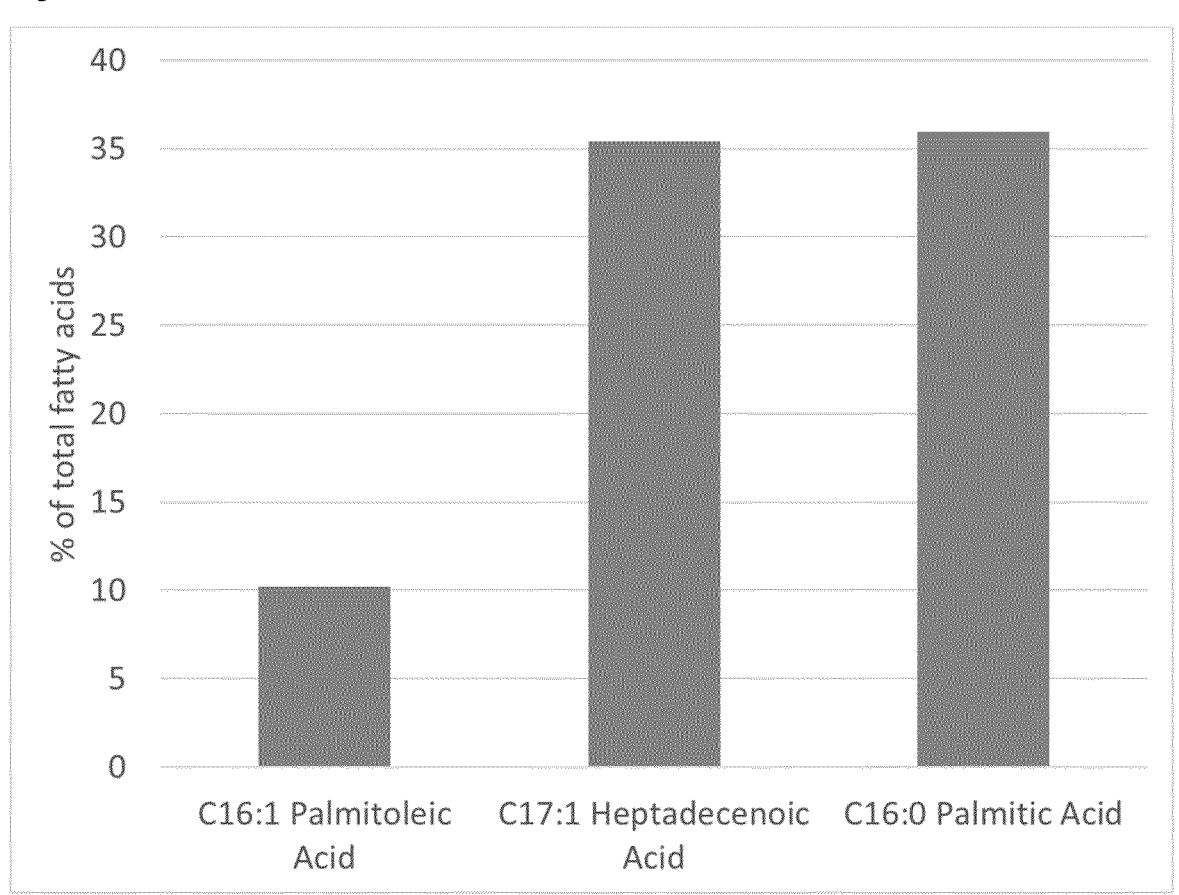
FIG. 3 shows an example of the proportions of the most abundant fatty acids of the total fatty acid content of isolated biomass produced according to the method of the invention.

FIG. 3 shows an example of the proportions of the most abundant fatty acids of the total fatty acid content of isolated biomass produced according to the method of the invention. The fatty acid content of isolated biomass produced according to the method of the invention is determined by the following method:

Samples are heated under reflux for 2 hours with a mixture of Methanol and Sulfuric acid in Toluene. Fats and Oils are trans-esterified to Fatty Acid Methyl Esters (FAMES). A small volume of n-Hexane is used to extract the resultant methyl ester mixture. Anhydrous Sodium Sulfate is then used to dry the n-Hexane solution before transferring the sample to a chromatography vial. FAMES fatty acid profiles are obtained by Gas-Liquid Chromatography using an FFAP column (dimensions 25 m×0.20 mm ID) with detection by Flame Ionisation Detector. Profiles may be reported with or without an internal standard (C17:0).

Figure 4:
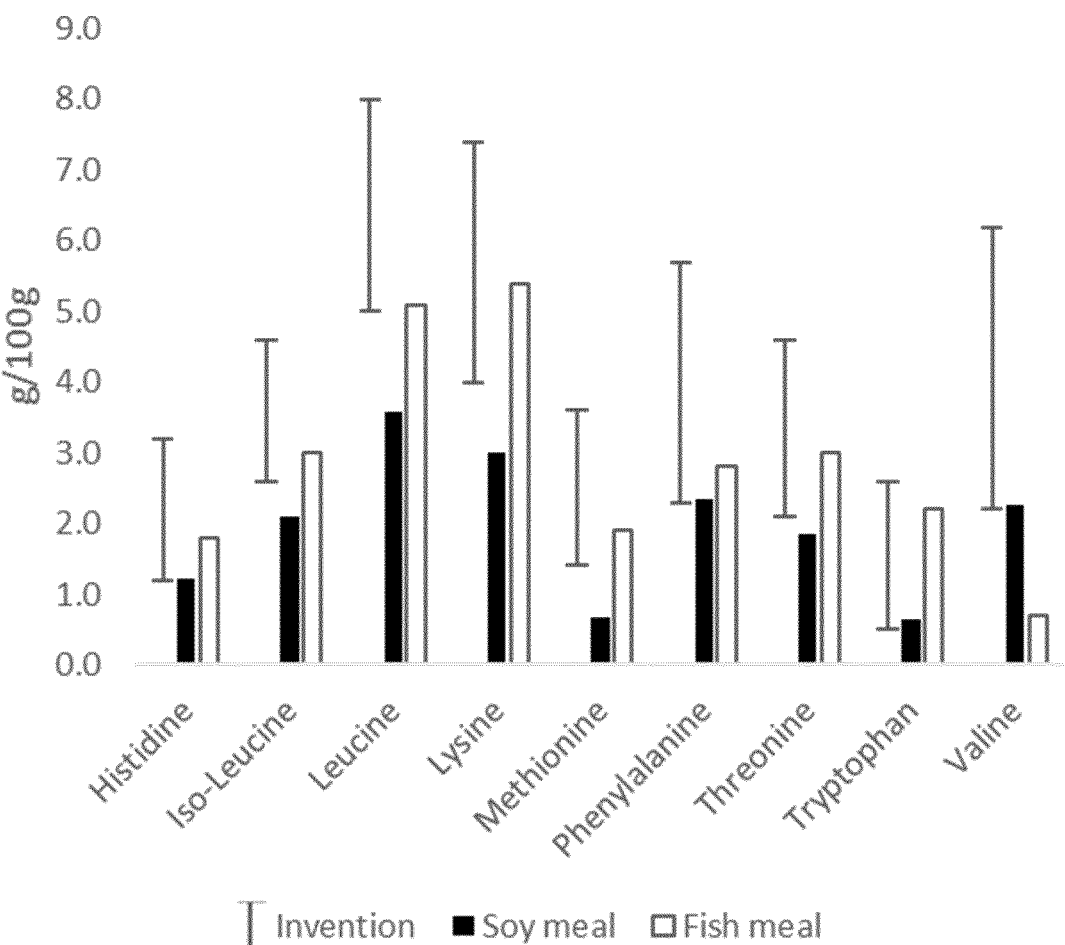
FIG. 4 shows an example of the ranges of amounts of the essential amino acids per 100 g of the total protein content of isolated biomass produced according to the method of the invention compared to those of typical soy meal and fish meal used in animal agriculture.

FIG. 4 shows an example of the ranges of amounts of the essential amino acids per 100 g of the total protein content of isolated biomass produced according to the method of the invention compared to those of typical soy meal and fish meal used in animal agriculture, see for instance U.S. Soybean Meal information flyer (accessed online on 20 Apr. 2020: https://ussec.org/wp-content/uploads/2015/10/US-Soybean-Meal-Information.pdf, issued by the US Soybean Export Council; and fish meal, see for instance M. Das and S. K. Mandal; Oxya hyla hyla (Orthoptera: Acrididae) as an Alternative Protein Source for Japanese Quail; International Scholarly Research Notices, 2014. The amino acid content of isolated biomass produced according to the method of the invention is determined by the following method:

A sample is oxidised in a combination of phenol, hydrogen peroxide, and formic acid. The oxidised sample is then hydrolysed with hydrochloric acid. Amino acids are subsequently separated using ion exchange chromatography and determined by post column reaction with ninhydrin using photometric detection.

It can clearly be seen that the biomass produced according to the method of the invention is of superior quality.

Figure 5:
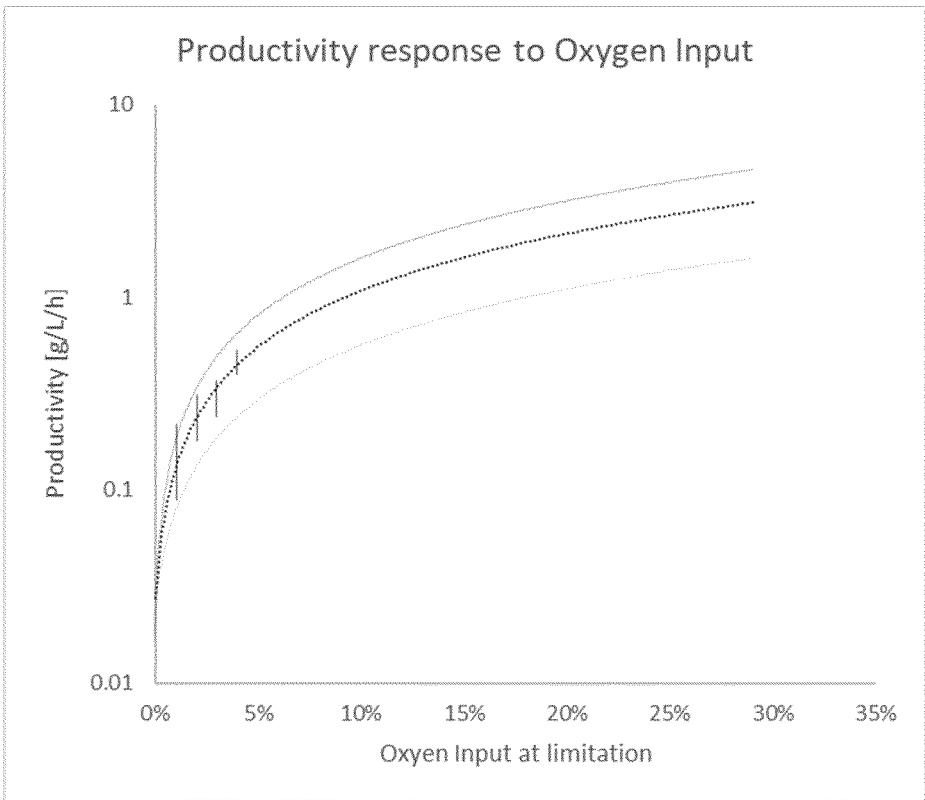
FIG. 5 shows a projection of biomass production rates at different input concentration percentages of oxygen (FIG. 5A) and hydrogen (FIG. 5B).
Figure 5:
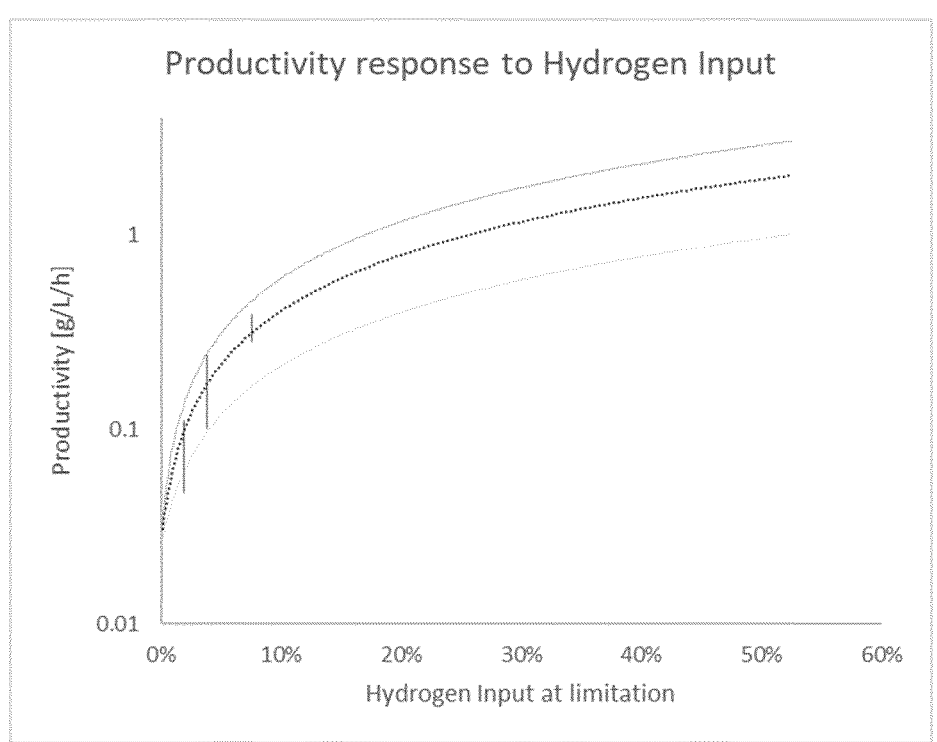

FIGS. 5A and B show a projection of biomass production rates at different input concentration percentages of oxygen and hydrogen. The oxygen and hydrogen concentrations are of those added to the liquid phase and biomass production rates are those of biomass with at least 65% protein resulting in a biomass production rate of more than 10 g/l/d from specific concentration percentages and up of respectively oxygen (FIG. 5 A) or hydrogen (FIG. 5 B). FIG. 5A is limited with regard to amount of substrates other than oxygen such that they are provided at a minimum amount sufficient for viability of the microorganisms. FIG. 5 B is limited with regard to amount of substrates other than hydrogen such that they are provided at a minimum amount sufficient for viability of the microorganisms.

Figure 6:
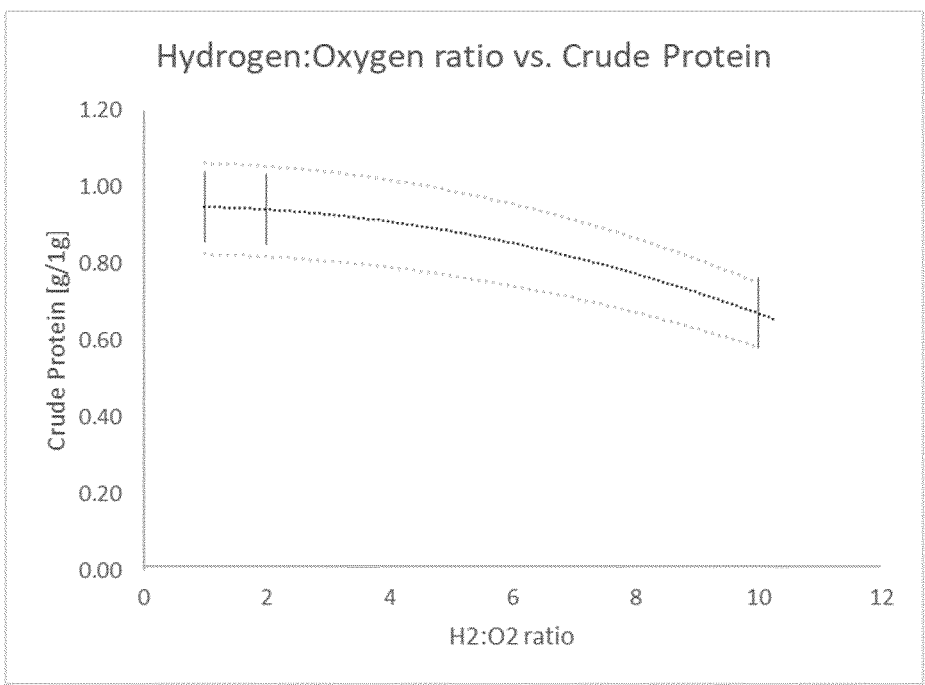
FIG. 6 shows a projection of protein content of total biomass by dry weight from hydrogen-oxidising microorganisms produced according to the invention, wherein controlling the input stream comprises adding a molar ratio of hydrogen:oxygen in the liquid phase.

FIG. 6 shows a projection of protein content of total biomass by dry weight from hydrogen-oxidising microorganisms produced according to the invention, wherein controlling the input stream comprises adding a molar ratio of hydrogen:oxygen in the liquid phase of from 1:1 to 10:1, resulting in a biomass production rate of more than 10 g/l/d.

Figure 7:
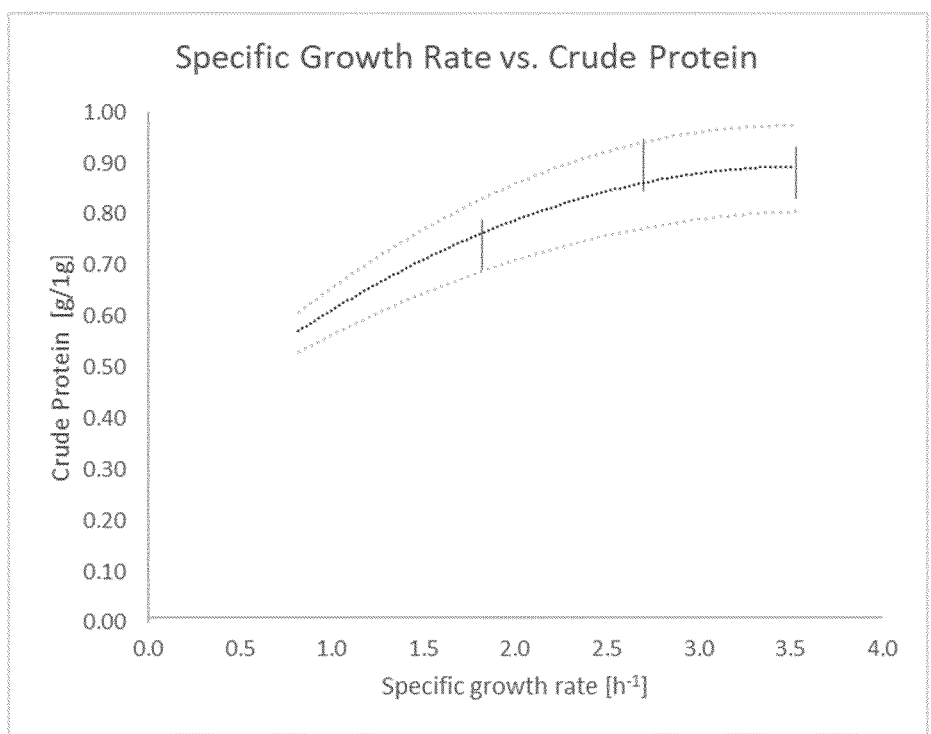
FIG. 7 shows a projection of protein content of total biomass by dry weight from hydrogen-oxidising microorganisms produced according to the invention, wherein controlling the input stream comprises controlling the specific growth rate.

FIG. 7 shows a projection of protein content of total biomass by dry weight from hydrogen-oxidising microorganisms produced according to the invention, wherein controlling the input stream comprises controlling the specific growth rate, resulting in a biomass production rate of more than 10 g/l/d.

FIG. 8A shows a projection of preferred hydrogen transfer rates in relation to biomass production rate produced according to the invention, wherein the biomass comprises at least 65% protein of total biomass by dry weight. The required hydrogen transfer rate for a target Productivity can be calculated by multiplying the Yield of hydrogen to biomass ($Y\_\{H2/X\}$) with the Productivity, where $Y\_\{H2/X\}$ is the g hydrogen used per gram biomass formed. FIG. 8A identifies the necessary mass transfers required to obtain productivities in excess of 10 g/L/d within the economically preferred metabolic yield range for Hydrogen which are attainable using the method according to the invention. FIG. 8 B shows a projection of preferred oxygen transfer rates in relation to biomass production rate produced according to the invention, wherein the biomass comprises at least 65% protein of total biomass by dry weight. The required hydrogen transfer rate for a target Productivity can be calculated by multiplying the Yield of oxygen to biomass ($Y\_\{O2/X\}$) with the Productivity, where $Y\_\{O2/X\}$ is the g oxygen used per gram biomass formed. FIG. 8B identifies the necessary mass transfers required to obtain productivities in excess of 10 g/L/d within the economically preferred metabolic yield range for Oxygen which are attainable using the method according to the invention.

The following, non-limiting examples illustrate the process and materials according to the invention.

Example 1

*Cupriavidis necator* strain H16, also known as DSM 428 (Little et al.: "Complete Genome Sequence of *Cupriavidis necator* H16 (DSM 428)"; Microbiol. Resour. Announc. (2019)) or previously known as *Ralstonia eutrophia* H16 (Pohlmann et al.: "Genome sequence of the bioplastic-producing "Knallgas" bacterium *Ralstonia eutrophia* H16"; Nature Biotechnology (2006)), is cultured according to the invention in an industrial chemostat bioreactor system as described in FIG. 1.

DSMZ mineral medium for chemolithotrophic growth 81 (H-3) is used, which consists of the following and is prepared as follows:

Solution A:

$KH_2PO_4$ 2.3 g, $Na_2HPO_4 \times 2\ H_2O$ 2.9 g, Distilled water 50 ml

Solution B:

$NH_4Cl$ 1.0 g, $MgSO_4 \times 7\ H_2O$ 0.50 g, $CaCl_2 \times 2\ H_2O$ 0.01 g, $MnCl_2 \times 4\ H_2O$ 0.005 g, $NaVO_3 \times H2O$ 0.005 g, Trace element solution SL-6 5 ml, Distilled water 915 ml Solution C:

Ferric Ammonium Citrate 0.05 g, Distilled Water 20 ml

Solutions A, B, C are autoclaved separately for 15 min at 121° C., cooled down to 50° C. and then mixed aseptically with 5.0 ml filter-sterilized standard vitamin solution (see below). The pH of this medium is adjusted to a pH between 1 and 4 and supplemented with an additional 1.5 g/L ammonium chloride, $3 \times 10^{-4}$ g/L $NiCl_2 \times 6H_2O$, and $1.5 \times 10^{-3}$ g/L $ZnSO_4 \times 7H_2O$, and $1.5 \times 10^{-4}$ g/L $CuCl_2 \times 2H_2O$, and 0.15 g/L Ferric ammonium citrate. With the above medium and preparation method it is possible to support an operating concentration of biomass which contains more than 65% protein at more than 10 g/L cell dry weight basis under gas limiting growth conditions and productivities of more than 10 g/L/d where in addition in situ pH control is employed using an appropriate base, for example 0.2M NaOH or $NH_4OH$. In order to support higher operating cell concentrations and productivities the medium ingredients can be scaled proportionally.

Standard Vitamin Solution:

Riboflavin 10 mg, Thiamine-HCl×2 $H_2O$ 50 mg, Nicotinic acid 50 mg, Pyridoxine-HCl 50 mg, Ca-pantothenate 50 mg, Biotin 0.1 mg, Folic acid 0.2 mg, Vitamin B12 1.0 mg, Distilled water 100 ml Trace Element Solution SL-6:

$ZnSO_4 \times 7\ H_2O$ 0.10 g, $MnCl_2 \times 4\ H_2O$ 0.03 g, $H_3BO_3$ 0.30 g, $CoCl_2 \times 6\ H_2O$ 0.20 g, $CuCl_2 \times 2\ H_2O$, 0.01 g, $NiCl_2 \times 6\ H_2O$ 0.02 g, $Na_2MoO_4 \times 2\ H_2O$ 0.03 g, Distilled water 1000 ml The culture is grown for at least 3 days under constant agitation of the culture medium. Carbon dioxide gas is added to the liquid phase in a non-limiting concentration. Hydrogen and oxygen gas are added to the liquid phase in a ratio of from 1:1 to 10:1. The gaseous substrates are optionally recycled. The liquid culture medium is recycled. Nutrient compounds and culture medium are added and part of the liquid phase is removed from the system during culture. The total volume of the liquid phase is maintained more or less constant. Gas transfer rates are used according to the preferred rates as indicated in FIGS. 8 A and 8 B.

Biomass was produced and isolated according to the invention resulting in biomass with an amino acid content of FIG. 2 and a fatty acid content of FIG. 3 and table 1 below.

TABLE 1

| Fatty Acid | % (of Total Fatty Acids) |
|---|---|
| C08:0 Caprylic Acid | 0.09 |
| C12:0 Lauric Acid | 0.1 |
| C10:0 Capric Acid | 0.11 |
| C18:2 Linoleic Acid | 0.14 |
| C18:1 Oleic Acid | 0.25 |
| C14:1 Myristoleic Acid | 0.26 |
| C18:0 Stearic Acid | 0.41 |
| C18:3 Linolenic Acid | 1.6 |
| C14:0 Myristic Acid | 4.22 |
| C16:1 Palmitoleic Acid | 10.19 |
| C17:1 Heptadecenoic Acid | 35.41 |
| C16:0 Palmitic Acid | 35.96 |

Example 2

A *Cupriavidis necator* strain is cultured in an industrial bioreactor system as described in FIG. 1 using the culture conditions as described in example 1. The dilution rate is 2 d$^{-1}$ in FIGS. 5A and 1 d$^{-1}$ in FIG. 5 B.

The result is productivity with different hydrogen/oxygen inputs at limitation as shown in FIGS. 5A and 5 B and extrapolated from the experimental results. Protein content is at least 65%.

Example 3

A *Cupriavidis necator* strain is cultured in an industrial bioreactor system as described in FIG. 1 using the culture conditions as described in example 1. The dilution rate is 1.87 d$^{-1}$.

The result is protein content with different hydrogen: oxygen input ratios as shown in FIG. 6 and extrapolated from the experimental results. Productivity of biomass is at a rate greater than 10 g/l/d.

Example 4

A *Cupriavidis necator* strain is cultured in an industrial bioreactor system as described in FIG. 1 using the culture conditions as described in example 1. The dilution rate for the three points is from left to right respectively 1.82, 2.70 and 3.53 d$^{-1}$. The H2:O2 ratio is 2:1.

The result is protein content with different specific growth rates as shown in FIG. 7 and extrapolated from the experimental results. Productivity of biomass is at a rate greater than 10 g/l/d.

Example 5

A *Cupriavidis necator* strain is cultured in an industrial bioreactor system as described in FIG. 1 using the culture conditions as described in example 1.

The result is productivity with different hydrogen transfer rates as shown in FIG. 8A and extrapolated from the experimental results in the table below. Protein content is at least 65%.

Example 6

A *Cupriavidis necator* strain is cultured in an industrial bioreactor system as described in FIG. 1 using the culture conditions as described in example 1.

The result is productivity with different oxygen transfer rates as shown in FIG. 8 B and extrapolated from the experimental results. Protein content is at least 65%.

The invention claimed is:

1. A continuous method for producing a biomass comprising at least 65% protein of total biomass by dry weight from hydrogen-oxidizing microorganisms comprising bacteria selected from the genus *Cupriavidus* sp, using one or more input streams comprising one or more gaseous substrates, comprising hydrogen and oxygen, the method comprising:

contacting the microorganisms in a liquid phase with a nutrient composition comprising nitrogen and phosphorous-comprising compounds and the gaseous substrates, wherein the one or more gaseous substrates comprises carbon dioxide, or wherein the nutrient composition comprises carbon-comprising compounds, and wherein the input stream and nutrient composition are controlled and wherein the biomass is produced at a rate of more than 10 g/l/d, the method further comprising:

i. controlling the input stream comprising adding a molar ratio of hydrogen: oxygen to the liquid phase of from 1:1 to 10:1;

ii. controlling the input stream and nutrient composition comprising maintaining a specific growth rate of the microorganisms of from 1.0 to 8.0 d$^{-1}$ or from 0.04 to 0.3 h$^{-1}$;

iii. controlling the input stream comprising maintaining hydrogen at a transfer rate of from 0.03 to 1.2 mol/l/h in the liquid phase or oxygen at a transfer rate of from 0.003 to 0.4 mol/l/h in the liquid phase; and iv. replacing the liquid phase of the bioreactor where the microorganisms are grown and maintained at a volume of from 4 to 30% per hour; wherein a microbial concentration of at least 10 g/l is maintained in the liquid phase.

2. The method of claim 1, wherein controlling the input stream comprises adding hydrogen in a concentration of from 70 to 100% (v/v), oxygen in a concentration of from 20 to 100% (v/v) and carbon dioxide in a concentration of from 5 to 100% (v/v) to the liquid phase, individually or as any premixed combination thereof.

3. The method of claim 1, wherein controlling the input stream and nutrient composition comprises maintaining a concentration of the microorganisms in the liquid phase of the bioreactor, wherein the concentration comprises at least 10 g/l.

4. The method of claim 1, wherein controlling the input stream and nutrient composition comprises maintaining a concentration of the microorganisms in the liquid phase of the bioreactor, wherein the concentration comprises from 10 g/l to 100 g/l.

5. The method of claim 1, wherein controlling the input stream comprises adding a molar ratio of hydrogen:oxygen: carbon dioxide of from 3.88 to 51.94:0.85 to 2:0.75 to 2 to the liquid phase.

6. The method of claim 1, wherein controlling the input stream comprises maintaining a molar ratio of dissolved hydrogen:oxygen:carbon dioxide of from 3.183 to 12.748: 0.795 to 4.25:0.75 to 2.0 in the liquid phase.

7. The method of claim 1, wherein controlling the input stream comprises maintaining a concentration of hydrogen of from 0.5 to 20 mg/l, a concentration of oxygen of from 0.5 to 80 mg/l and a concentration of carbon dioxide of from 20 to 2000 mg/l in the liquid phase at a temperature of from 28 to 45° C. and at a pressure in the gaseous phase of from 100 to 2000 kPa.

8. The method of claim 1, wherein controlling the input stream comprises maintaining a molar ratio of hydrogen: oxygen gas hold-up in the liquid phase of from 0.5:1 to 7:1 or from 1:1 to 3.5:1.

9. The method of claim 1, wherein the microorganisms utilize the hydrogen at a rate of from 0.05 to 0.5 mol/g/h, the oxygen at a rate of from 0.04 to 0.18 mol/g/h, and the carbon dioxide at a rate of from 0.03 to 0.13 mol/g/h.

10. The method of claim 1, wherein the carbon dioxide is derived from the exhaust gas of a production or combustion process.

11. The method of claim 10, wherein the carbon dioxide is purified and concentrated to a concentration of from 40 to 100% (v/v).

12. The method of claim 1, wherein the step of contacting the microorganisms in a liquid phase with a nutrient composition comprises adding a nutrient composition which is adjusted to a pH of from 1 to 4 prior to adding, wherein the nutrient composition comprises DSMZ medium for chemo-lithotrophic growth 81 (H-3) without $NaHCO_3$.

13. The method of claim 12 wherein, prior to adding, the medium is supplemented with an additional 1.5 g/L ammonium chloride, $3\times10^{-4}$ g/L $NiCl_2\times6H_2O$, and $1.5\times10^{-3}$ g/L $ZnSO_4\times7H_2O$, and $1.5\times10^{-4}$ g/L $CuCl_2\times2H_2O$, and 0.15 g/L Ferric ammonium citrate.

14. The method of claim 1, wherein the microorganisms comprise bacteria selected from the species *Cupriavidus necator.*

15. The method of claim 1 further comprising removing the nutrient composition and isolating the biomass produced by dewatering or drying the biomass such that the biomass comprises a water content of less than 5% by weight.

16. The method of claim 15 further comprising using the dried or dewatered nutrient composition removed by dewatering or drying the biomass as the nutrient composition for contacting the microorganisms in a liquid phase.

* * * * *